United States Patent
Helms et al.

(10) Patent No.: US 9,284,188 B2
(45) Date of Patent: Mar. 15, 2016

(54) CYTOSOLIC DELIVERY OF MATERIALS WITH ENDOSOME-DISRUPTING COLLOIDS

(75) Inventors: Brett A. Helms, San Francisco, CA (US); Andrea R. Bayles, New Canaan, CT (US)

(73) Assignee: The Regents of the University of California, Oakland, CA (US)

( * ) Notice: Subject to any disclaimer, the term of this patent is extended or adjusted under 35 U.S.C. 154(b) by 734 days.

(21) Appl. No.: 13/225,199

(22) Filed: Sep. 2, 2011

(65) Prior Publication Data

US 2012/0058505 A1   Mar. 8, 2012

Related U.S. Application Data

(60) Provisional application No. 61/380,169, filed on Sep. 30, 2010.

(51) Int. Cl.
| | |
|---|---|
| B82Y 5/00 | (2011.01) |
| C08F 265/06 | (2006.01) |
| C08F 265/10 | (2006.01) |
| B82Y 15/00 | (2011.01) |
| G01N 33/50 | (2006.01) |
| G01N 33/58 | (2006.01) |

(52) U.S. Cl.
CPC . *B82Y 5/00* (2013.01); *B82Y 15/00* (2013.01); *C08F 265/06* (2013.01); *C08F 265/10* (2013.01); *G01N 33/5005* (2013.01); *G01N 33/588* (2013.01)

(58) Field of Classification Search
CPC ........ B82Y 5/00; B82Y 15/00; C08F 256/00; C08F 256/10; C08F 265/06; C08F 265/10; C08L 51/04; C08L 51/003
USPC .......... 524/401, 439; 525/296, 302, 303, 304, 525/305, 308, 309, 902; 977/927, 779, 783
See application file for complete search history.

(56) References Cited

U.S. PATENT DOCUMENTS

| | | | |
|---|---|---|---|
| 4,036,882 A | 7/1977 | Bertozzi et al. | |
| 5,191,015 A | 3/1993 | Sheppard et al. | |
| 5,990,479 A | 11/1999 | Weiss et al. | |
| 6,207,392 B1 | 3/2001 | Weiss et al. | |
| 6,333,051 B1 | 12/2001 | Kabanov et al. | |
| 6,423,551 B1 | 7/2002 | Weiss et al. | |
| 6,699,723 B1 | 3/2004 | Weiss et al. | |
| 6,727,065 B2 | 4/2004 | Weiss et al. | |
| 6,927,069 B2 | 8/2005 | Weiss et al. | |
| 7,056,901 B2 | 6/2006 | Frechet et al. | |
| 7,101,718 B2 | 9/2006 | Weiss et al. | |
| 7,314,764 B2 | 1/2008 | Weiss et al. | |
| 7,683,041 B2 | 3/2010 | Frechet et al. | |
| 8,071,359 B2 | 12/2011 | Weiss et al. | |
| 8,071,360 B2 | 12/2011 | Weiss et al. | |
| 8,071,361 B2 | 12/2011 | Weiss et al. | |
| 8,137,700 B2 | 3/2012 | Frechet et al. | |
| 6,423,551 C1 | 5/2012 | Weiss et al. | |
| 6,699,723 C1 | 5/2012 | Weiss et al. | |
| 6,927,069 C1 | 5/2012 | Weiss et al. | |
| 8,288,152 B2 | 10/2012 | Weiss et al. | |
| 8,288,153 B2 | 10/2012 | Weiss et al. | |
| 8,639,449 B2 | 1/2014 | Weiss et al. | |
| 2002/0072234 A1 | 6/2002 | Alivisatos et al. | |
| 2003/0099968 A1 | 5/2003 | Alivisatos et al. | |
| 2003/0100130 A1 | 5/2003 | Alivisatos et al. | |
| 2003/0113709 A1 | 6/2003 | Alivisatos et al. | |
| 2004/0254141 A1 | 12/2004 | Schinazi et al. | |
| 2005/0261490 A1 | 11/2005 | Perplies et al. | |
| 2006/0003464 A1 | 1/2006 | Alivisatos et al. | |
| 2006/0177945 A1 | 8/2006 | Alivisatos et al. | |
| 2007/0111350 A1 | 5/2007 | Alivisatos et al. | |
| 2009/0191567 A1 | 7/2009 | Alivisatos et al. | |
| 2009/0253211 A1 | 10/2009 | Alivisatos et al. | |
| 2010/0155668 A1 | 6/2010 | Alivisatos et al. | |
| 2010/0224853 A1 | 9/2010 | Alivisatos et al. | |
| 2011/0275169 A1 | 11/2011 | Alivisatos et al. | |

FOREIGN PATENT DOCUMENTS

| | | |
|---|---|---|
| CA | 2366303 | 9/2000 |
| DE | 600 48 188.3 | 2/2011 |
| EP | 2287614 | 2/2011 |
| FR | 2287614 | 2/2011 |
| GB | 2287614 | 2/2011 |
| JP | 4601828 | 12/2010 |

OTHER PUBLICATIONS

Lynn, D. M.; Anderson, D. G.; Putnam, D.; Langer, R. J. Am. Chem. Soc. 2001, 123, 8155.

Akinc, A.; Anderson, D. G.; Lynn, D. M.; Langer, R. Bioconjugate Chem. 2003, 14, 979.

Yezhelyev, M. V.; Qi, L.; O'Regan, R. M.; Nie, S.; Gao, X. J. Am. Chem. Soc. 2008, 130, 9006.

Davda, J.; Labhasetwar, V. Int. J. Pharm. 2002, 233, 51.

Fischer, D.; Li, Y.; Ahlemeyer, B.; Krieglstein, J.; Kissel, T. Biomaterials 2003, 24, 1121.

Hong, S.; Bielinska, A. U.; Mecke, A.; Keszler, B.; Beals, J. L; Shi, X.; Balogh, L; Orr, B. G.; Baker, J. R.; Banaszak Holl, M. M. Bioconjugate Chem. 2004, 15, 774.

(Continued)

*Primary Examiner* — Robert Jones, Jr.

(74) *Attorney, Agent, or Firm* — Michelle Chew Wong; Lawrence Berkeley National Laboratory

(57) ABSTRACT

A facile procedure to deliver nanocrystals to the cytosol of live cells that is both rapid and general. The technique employs a unique cationic core-shell polymer colloid that directs nanocrystals to the cytosol of living cells within a few hours of incubation. The present methods and compositions enable a host of advanced applications arising from efficient cytosolic delivery of nanocrystal imaging probes: from single particle tracking experiments to monitoring protein-protein interactions in live cells for extended periods.

17 Claims, 7 Drawing Sheets

(56) References Cited

OTHER PUBLICATIONS

Bēma, D.; Freivalds, T.; Buikis, I.; Harju, L. In 14th Nordic-Baltic Conference on Biomedical Engineering and Medical Physics, 2008, pp. 598-601.
Zhang, X.; Jin, Y.; Plummer, M. R.; Pooyan, S.; Gunaseelan, S.; Sinko, P. J. Mol. Pharmaceutics 2009, 6, 836.
Zhang, S.; Li, J.; Lykotrafitis, G.; Bao, G.; Suresh, S. Adv. Mater. 2009, 21, 419.
Beaudette, T. T.; Cohen, J. A.; Bachelder, E. M.; Broaders, K. E.; Cohen, J. L.; Engleman, E. G.; Fréchet J. M. J. J. Am. Chem. Soc. 2009, 131, 10360.
Scita, G.; Di Fiore, P. P. Nature 2010, 463, 464.
Amalvy, J. I.; Unali, G.; Li, Y.; Granger-Bevan, S.; Armes, S. P.; Binks, B. P.; Rodrigues, J. A.; Whitby, C. P. Langmuir 2004, 20, 4345.
Amalvy, J. I.; Wanless, E. J.; Li, Y.; Michailidou, V.; Armes, S. P.; Duccini, Y. Langmuir 2004, 20, 8992.
Hu, Y.; Litwin, T.; Nagaraja, A. R.; Kwong, B.; Katz, J.; Watson, N.; Irvine, D. J. Nano Lett. 2007, 7, 3056.
You, J.-O.; Auguste, D. T. Nano Lett. 2009, 9, 4467.
Hu, Y.; Atukorale, P. U.; Lu, J. J.; Moon, J. J.; Um, S. H.; Cho, E. C.; Wang, Y.; Chen, J.; Irvine, D. J. Biomacromolecules 2009, 10, 756.
Derfus, A. M.; Chan, W. C. W.; Bhatia, S. N. Nano Lett. 2004, 4, 11.
Hoshino, A.; Fujioka, K.; Oku, T.; Suga, M.; Sasaki, Y. F.; Ohta, T.; Yasuhara, M.; Suzuki, K; Yamamoto, K. Nano Lett. 2004, 4, 2163.
Lovrić, J.; Cho, S. J.; Winnik, F. M.; Maysinger, D. Chem. Biol. 2005, 12, 1227.
Kirchner, C.; Liedl, T.; Kudera, S.; Pellegrino, T.; Javier, A. M.; Gaub, H. E.; Stölzle, S.; Fertig, N.; Parak, W. J. Nano Lett. 2005, 5, 331.
Ryman-Rasmussen, J. P.; Riviere, J. E.; Monteiro-Riviere, N. A. Nano Lett. 2007, 7, 1344.
Anseth et al., "Photopolymerizable Degradable Polyanhydrides with Osteocompatibility," Nature Biotechnology, vol. 17, p. 156-159, (Feb. 1999).
Anseth et al., "In Situ Forming Degradable Networks and Their Application in Tissue Engineering and Drug Delivery," Journal of Controlled Release, vol. 78, p. 199-209, (2002).
Apostolopoulos et al., "Role of Mannose Receptor in the Immune Response," Current Molecular Medicine, vol. 1 ( No. 4), p. 469-474, (2001).
Behravesh et al., "Synthesis of in Situ Cross-Linkable Macroporous Biodegradable Poly(propylene fumarate-co-ethylene glycol) Hydrogels," Biomacromolecules, vol. 3 (No. 2), p. 374-381, (Feb. 6, 2002).
Daubreese et al., "Synthesis and Inverse Emulsion Polymerization of Aminated Acrylamidodextran," J. Pharm. Pharmacol., vol. 45, p. 1018-1023, (1993).
Delgado, "A Tunable Hydrogel for Encapsulation and Controlled Release of Bioactive Proteins," Biomacromolecules, vol. 3 ( No. 2), p. 262-271, (Dec. 21, 2001).
Garcia Del Barrio, "Loading of Plasmid DNA into GIGA Microparticles Using TROMS (Total Recirculation One-Machine System): Evaluation of its Integrity and Controlled Release Properties," Journal of Controlled Release, vol. 86, p. 123-130, (2003).
Helmlinger, "Acid Production in Glycolysis-impaired Tumors Provides New Insight into Tumor Metabolism," Clinical Cancer Research, vol. 8, p. 1284-1291, (Apr. 2002).
Hoffman, "Hydrogels for Biomedical Applications," Annals New York Academy of Science, vol. 944, p. 62-73, (2001).
Lu et al., "Release Behavior of High Molecular Weight Solutes from Poly(ethyleneglycol)-Based Degradable Networks," Macromolecules, vol. 33 ( No. 7), p. 2509-2515, (Mar. 15, 2000).
Lynn et al., "pH-Responsive Polymer Microspheres: Rapid Release of Encapsulated Material within the Range of Intracellular pH," Angew. Chem. Int. Ed., vol. 40 (No. 9), p. 1707-1710, (2001).
Murthy et al., "A Novel Strategy for Encapusulation and Release of Proteins: Hydrogels and Microgels with Acid-Labile Acetal Cross-Linkers," Journal of American Chemical Society, vol. 124 (No. 42), p. 12398-1239, (2002).
O'Hagan et al., "Poly(lactide-co-glycolide) microparticles for the development of single-does controlled-released vaccines," Advanced Drug Delivery Reviews, vol. 32, p. 225-246, (1998).
Park, "Temperature Modulated Protein Release from pH/temperature-sensitive Hydrogels," Biomaterials, vol. 20, p. 517-521, (1999).
Park et al., "Controlled Release of Clot-Dissolving Tissue-Type Plasminogen Activator from a ploy(L-glutamic acid) semi-interpenetrating polymer network hydrogel," Journal of Controlled Release, vol. 75, p. 37-44, (2001).
Ruckenstein, "A Novel Breakable Cross-Linker and pH-Responsive Star-Shaped and Gel Polymers," Macromolecules, vol. 32 (No. 12), p. 3979-3983, (May 17, 1999).
Sassi et. al., "Partitioning of Proteins and Small Biomolecules in Temperature-and pH-sensitive Hydrogels," Polymer, vol. 37 (No. 11), p. 2151-2164, ( 1996).
Sawhney et al., "Bioerodible Hydrogels Based on Photopolymerized Poly(ethyleneglycol)-co-poly(a-hydroxy acid) Diacrylate Macromers," Macromolecules, vol. 26 (No. 4), p. 581-587, (1993).
Trevani et al., "Extraceullar Acidification Induces Human Neutrophil Activation," The Journal of Immunology, vol. 162, p. 4849-4857, (Jan. 14, 1999).
Qi, L.; Gao, X. ACS Nano, 2008, 2, 1403.
Bystricky et al., "Candida albicans mannan/ protein conjugate as vaccine candidate." Immunology Letters, 2003, vol. 85, pp. 251-255.
Bystricky et al., "Conjugation of yeast mannans with protein employing cyanopyridinium agent (CDAP)—an effective route of antifungal vaccine preparation." Glycoconjugate Journal, 2000, vol. 17, pp. 677-680.
Van Dijk-Wolthuis, W.N.E. et al, Degradation and Release Behavoir of Dextran-Based Hydrogels, Macromolecules 1997, 30, 4639-4645.
Ruckenstein et al., Macromolecules, 32, 3979-83 (1997).
Salomaa, P., The Acid-Catalysed Solvolysis of Alkoxymethyl Esters. Part IV. The Temperature Dependence of the Hydrolysis Rate, Acta Chemica Scandinavica, 11 (1957) 239-246.
Gillies et al, Bioconjugate Chem 2004, 15, 1254-1263.
K. E. Broaders, J. A. Cohen, T. T. Beaudette, E. M. Bachelder, J. M. J. Fréchet, Proc. Nat. Acad. Sci. U.S.A. 2009, 106, 5497.
D. M. Lynn, R. Langer, J. Am. Chem. Soc. 2000, 122, 10761.
Witschi et al (Pharmaceutical Research, 16(3):382-390, 1999).
A. Akinc, D. M. Lynn, D. G. Anderson, R. Langer, J. Am. Chem. Soc. 2003, 125, 5316.
E. M. Bachelder, T. T. Beaudette, K. E. Broaders, S. E. Paramonov, J. Dashe, J. M. J. Fréchet, Mol. Pharmaceutics 2008, 5, 876.
S. E. Paramonov, E. M. Bachelder, T. T. Beaudette, S. M. Standley, C. C. Lee, J. Dashe, J. M. J. Fréchet, Bioconjugate Chem. 2008, 19, 911.
E. M. Bachelder, T. T. Beaudette, K. E. Broaders, J. Dashe, J. M. J. Fréchet, J. Am. Chem. Soc. 2008, 130, 10494.
Berridge, M. J.; Lipp, P.; Bootman, M. D. Nat. Rev. Mol. Cell Biol. 2000, 1, 11.
Zhang, J.; Campbell, R. E.; Ting, A. Y.; Tsien, R. Y. Nat. Rev. Mol. Cell Biol. 2002, 3, 906.
Jan, L. Y.; Siegelbaum, S. A. Curr. Opin. Neurobiol. 2005, 15, 253.
Jørgensen, C.; Linding, R. Curr. Opin. Genetics Dev. 2010, 20, 15.
Lee, K. H.; Lee, S.; Lee, W. Y.; Yang, H. W.; Heo, W. D. Proc. Nat. Acad. Sci. U.S.A. 2010, 107, 3412.
Yarden, Y.; Sliwkowski, M. X. Nat. Rev. Mol. Cell Biol. 2001, 2, 127.
Wu, X.; Liu, H.; Liu, J.; Haley, K. N.; Treadway, J. A.; Larson, J. P.; Ge, N.; Peale, F.; Bruchez, M. P. Nat. Biotechnol. 2003, 21, 41.
Gao, X.; Cui, Y.; Levenson, R. M.; Chung, L. W. K.; Nie, S. Nat. Biotechnol. 2004, 22, 969.
Alivisatos, A. P. Science 1996, 271, 933.
Bruchez, M.; Moronne, M.; Gin, P.; Weiss, S.; Alivisatos, A. P. Science 1998, 281, 2013.
Chan, W. C. W.; Nie, S. Science 1998, 281, 2016.
Michalet, X.; Pinaud, F.; Lacoste, T. D.; Dahan, M.; Bruchez, M. P.; Alivisatos, A. P.; Mitchell, P. Nat. Biotechnol.
Michalet, X.; Pinaud, F.; Lacoste, T. D.; Dahan, M.; Bruchez, M. P.; Alivisatos, A. P.; Weiss, S. Single Molecules 2001, 2, 261.
Parak, W. J.; Gerion, D.; Pellegrino, T.; Zanchet, D.; Micheel, C.; Williams, S. C.; Boudreau, R.; Gros, M. A. L.; Larabell, C. A.; Alivisatos, A. P. Nanotechnology 2003, 14, R15.
Alivisatos, A. P. Nat. Biotechnol. 2004, 22, 47.

(56) References Cited

OTHER PUBLICATIONS

So, M.-K.; Xu, C.; Loening, A. M.; Gambhir, S. S.; Rao J. Nat. Biotechnol. 2006, 24, 339.

Weissleder, R.; Kelly, K.; Sun, E. Y.; Shtatland, T.; Josephson, L. Nat. Biotechnol. 2005, 23, 1418.

Somers, R. C.; Bawendi, M. G.; Nocera, D. G. Chem. Soc. Rev. 2007, 36, 579.

Resch-Genger, U.; Grabolle, M.; Cavaliere-Jaricot, S.; Nitschke, R.; Nann, T. Nat. Methods 2008, 5, 763.

Stephens, D. J.; Pepperkok, R.; Proc. Nat. Acad. Sci. U.S.A. 2001, 98, 4295.

Michalet, X.; Pinaud, F. F.; Bentolila, L. A.; Tsay, J. M.; Doose, S.; Li, J. J.; Sundaresan, G.; Wu, A. M.; Gambhir, S. S.; Weiss, S. Science 2005, 307, 538.

Chen, X.; Kis, A.; Zettl, A.; Bertozzi, C. R. Proc. Nat. Acad. Sci. U.S.A. 2007, 104, 8218.

Ruan, G.; Agrawal, A.; Marcus, A. I.; Nie, S. J. Am. Chem. Soc. 2007, 129, 14759.

Kim, B. Y. S.; Jiang, W.; Oreopoulos, J.; Yip, C. M.; Rutka, J. T.; Chan, W. C. W. Nano Lett. 2008, 8, 3887.

Brandenburg, B.; Zhuang, X. Nat. Rev. Microbiol. 2007, 5, 197.

Jaiswal, J. K.; Mattoussi, H.; Mauro, J. M.; Simon, S. M. Nat. Biotechnol. 2003, 21, 47.

Derfus, A. M.; Chan, W.; Bhatia, S. Adv. Mater. 2004, 16, 961.

Rozenzhak, S. M.; Kadakia, M. P.; Caserta, T. M.; Westbrook, T. R.; Stone, M. O.; Naik, R. R. Chem. Commun. 2005, 2217.

Delehanty, J. B.; Medintz, I. L.; Pons, T.; Brunel, F. M.; Dawson, P. E.; Mattoussi, H. Bioconjugate Chem. 2006, 17, 920.

Duan, H.; Nie, S. J. Am. Chem. Soc. 2007, 129, 3333.

Ruan, G.; Agrawal, A.; Marcus, A. I.; Nie, S. J. Am. Chem. Soc., 2007, 129, 14759.

Medintz, I. L.; Pons, T.; Delehanty, J. B.; Susumu, K.; Brunel, F. M.; Dawson, P. E.; Mattoussi, H. Bioconjugate Chem. 2008, 19, 1785.

Joo, K.; Lei, Y.; Lee, C.; Lo, J.; Xie, J.; Hamm-Alvarez, S. F.; Wang, P. ACS Nano 2008, 2, 1553.

Rajan, S. S.; Liu, H. Y.; Vu, T. Q. ACS Nano, 2008, 2, 153.

Anas, A.; Okuda, T.; Kawashima, N.; Nakayama, K.; Itoh, T.; Ishikawa, M.; Biju, V. ACS Nano, 2009, 3, 2419.

Wu, S.; Han, G.; Milliron, D. J.; Aloni, S.; Altoe, V.; Talapin, D. V.; Cohen, B. E.; Schuck, P. J. Proc. Nat. Acad. Sci. U.S.A. 2009, 106, 10917.

a)

b)

c)

US 9,284,188 B2

CYTOSOLIC DELIVERY OF MATERIALS WITH ENDOSOME-DISRUPTING COLLOIDS

CROSS-REFERENCE TO RELATED APPLICATIONS

This application claims priority to U.S. Provisional Patent Application Ser. No. 61/380,169, filed on Sep. 3, 2010, hereby incorporated by reference in its entirety.

STATEMENT OF GOVERNMENTAL SUPPORT

This invention was made during work supported by U.S. Department of Energy under Contract No. DE-AC02-05CH11231. The government has certain rights in this invention.

REFERENCE TO SEQUENCE LISTING, TABLE, OR COMPUTER PROGRAM

The instant application contains a Sequence Listing which has been submitted in ASCII format via EFS-Web and is hereby incorporated by reference in its entirety. Said ASCII copy, created on Sep. 2, 2011, is named 2849US_SequenceListing_ST25.txt and is 300 bytes in size.

BACKGROUND OF THE INVENTION

1. Field of the Invention

The present invention relates to polymer colloids, and methods for cytosolic delivery of materials such as luminescent nanoparticles.

2. Related Art

Luminescent nanocrystals hold great potential for bioimaging because of their exceptional optical properties, but their use in live cells has been limited. One of the major challenges in applying luminescent nanocrystals as probes for cellular imaging has been the difficulty of using them inside of live cells. While nanocrystals have exceptional optical properties and hold great potential as probes of these pathways, they have difficulty in reaching subcellular targets. Nanocrystals are typically taken up by cells via endocytosis and the large majority remains trapped in endosomes and vesicles, unable to reach the cytosol. Staining patterns are characteristically punctuate and often bright enough to obscure nanocrystal luminescence elsewhere.

This vesicular sequestration is persistent and precludes nanocrystals from reaching intracellular targets. Microinjection and other techniques have been used as an endgame around this problem; however, these processes are labor intensive, low throughput and frequently kill the treated cell. Molecular engineering of nanocrystal surface passivation, via TAT or other cell penetrating peptide motifs, has also not afforded an efficient mechanism of release from endosomes.

BRIEF SUMMARY OF THE INVENTION

The present invention provides for a method to deliver nanocrystals to the cytosol of live cells that is both rapid and general. The present technique employs a unique, cationic core-shell polymer colloid that directs nanocrystals to the cytosol of living cells within a few hours of incubation. When vesicles containing nanocrystals transported into the cell by these colloids fuse with lysosomes, the intraorganelle pH decreases causing the colloids to expand in volume due to a proton sponge constructed at their cores. Membrane disruption ensues, leaving nanocrystals free to disperse in the cytosol for imaging experiments.

The present invention further provides a composition comprising a polymer colloid for delivery of materials to the cytosol of live cells. The polymer colloid is preferably a cationic core-shell polymer colloid having a core that exhibits rapid expansion at low intraorganelle pH to facilitate the delivery of luminescent nanocrystal cargo into the cytosol of live cells.

In one embodiment, a composition comprising a nanocrystal-cationic core-shell polymer colloid comprising a core polymer having an outer shell and a nanocrystal conjugated to or coating the shell, wherein the core of the cationic core-shell polymer colloid comprising a polymer of core monomers, wherein a first core monomer, having the formula $R_1C(CH_2)—C(O)—R_2—R_3—N(R_4)R_5$, wherein $R_1$ is H or alkyl, $R_2$ is O or NH, $R_3$ is an alkyl and $R_4$ and $R_5$ are H or alkyl, is crosslinked to a second core monomer, having the formula $R_1C(CH_2)—C(O)—R_2—CH_2—(CH_2—O—CH_2)_n—CH_2—R_2—C(O)—C(CH_2)—R_1$, wherein $R_1$ is H or alkyl, $R_2$ is O or NH, and n is 1 to 50; wherein outer shell comprising polymer of shell monomer and core monomers, wherein the shell monomer having the formula $R_1C(CH_2)—C(O)—R_2—R_3—N(R_4)R_6$, wherein $R_1$ is H or alkyl, $R_2$ is O or NH, $R_3$ is an alkyl, $R_4$ is H or alkyl, and $R_6$ is H, alkyl, acyl or $C=(NH)NH_2$ and a second shell monomer having the formula $R_1C(CH_2)—C(O)—R_2—CH_2—(CH_2—O—CH_2)_n—CH_2—R_2—C(O)—C(CH_2)R_1$, wherein $R_1$ is H or alkyl, $R_2$ is O or NH, and n is 1 to 50, wherein the second core monomer and second shell monomer can be the same or different; wherein the nanocrystal comprising a nanocrystal core and nanocrystal shell of any Groups I, II, III, VI, V, VI and/or lanthanide element and binary or ternary compounds, alloys or mixtures thereof.

In one aspect, the core of the cationic core-shell polymer colloid comprising a polymer of core monomers, wherein a first core monomer, having the formula $R_1C(CH_2)—C(O)—R_2—R_3—N(R_4)R_5$, wherein $R_1$ is H or alkyl, $R_2$ is O or NH, $R_3$ is an alkyl and $R_4$ and $R_5$ are H or alkyl, is crosslinked to a second core monomer, having the formula $R_1C(CH_2)—C(O)—R_2—CH_2—(CH_2—O—CH_2)_n—CH_2—R_2—C(O)—C(CH_2)—R_1$, wherein $R_1$ is H or alkyl, $R_2$ is O or NH, and n is 1 to 50. In some embodiments, the core monomers are provided as about 167 parts of a monomer having the formula $R_1C(CH_2)—C(O)—R_2—R_3—N(R_4)R_5$, wherein $R_1$ is methyl, $R_2$ is O, $R_3$ is an ethyl and $R_4$ and $R_5$ are ethyl, crosslinked to 1 part of a second core monomer having the formula $R_1C(CH_2)—C(O)—R_2—CH_2—(CH_2—O—CH_2)_n—CH_2—R_2—C(O)—C(CH_2)—R_1$, wherein $R_1$ is methyl, $R_2$ is O, and n is 3. Parts are suggested on a molar basis.

In another aspect, the shell comprising a first shell monomer having the formula $R_1C(CH_2)—C(O)—R_2—R_3—N(R_4)R_6$, wherein $R_1$ is H or alkyl, $R_2$ is O or NH, $R_3$ is an alkyl, $R_4$ is H or alkyl, and $R_6$ is H, alkyl, acyl or $C=(NH)NH_2$ and a second shell monomer having the formula $R_1C(CH_2)—C(O)—R_2—CH_2—(CH_2—O—CH_2)_n—CH_2—R_2—C(O)—C(CH_2)R_1$, wherein $R_1$ is H or alkyl, $R_2$ is O or NH, and n is 1 to 50, wherein the second core monomer and second shell monomer can be the same or different. Alternatively, the shell comprising a shell monomer having the formula $R_1C(CH_2)—CHO—R_2—R_7$, wherein $R_1$ is H or alkyl, $R_2$ is O or NH, and $R_7$ is H, alkyl, alkanols, oligoethyleneoxide and derivatives thereof, quaternary amino, alkyl phosphonates or alkylsulfonates.

In another aspect, the shell monomers of the colloid can be functionalized to provide further characteristics to the colloids. In some embodiments, the first or second shell monomer further comprising at least one pendant amine group whereby functional groups can be attached. In one embodiment, the functional group comprising a guanidine. In another aspect, the functional groups can be any polypeptide, antibody or other targeting sequence or agent which allows the colloid to be targeted to a subcellular area.

In another aspect, the nanoparticle further comprising functional ligands or coatings to affect or impart the nanoparticles with various properties including luminescence, solubility, hydrophobicity or hydrophilicity, targeting for specific subcellular, proteomic or genomic identification, etc. In one embodiment, the nanoparticle coating comprising streptavidin.

In one embodiment, the nanoparticle comprising a nanocrystalline matrix, such as $NaYF_4$, $ScF_3$, $YF_3$, $LaF_3$, $LaPO_4$, $YVO_4$, or $Y_2O_3$, doped with a suitable lanthanide or mixture of lanthanides. Suitable dopants include La, Ce, Pr, Nd, Pm, Sm, Eu, Gd, Tb, Dy, Ho, Er, Tm, and/or Yb.

In another aspect, the core monomer can be 2-(diethylamino)ethyl methacrylate (DEAEMA), 2-(dimethylamino) ethyl methacrylate, 2-(diisopropylamino)ethyl methacrylate, 2-(diethylamino)ethyl acrylate (DEAEMA), 2-(dimethylamino)ethyl acrylate, 2-(diisopropylamino)ethyl acrylate, 2-(diethylamino)ethyl acrylamide, 2-(dimethylamino)ethyl acrylamide, or 2-(diisopropylamino)ethyl acrylamide.

In another aspect, the second core monomer can be poly(ethylene glycol) dimethacrylate (PEGDMA), N,N'-[α,ω-diaminopoly(ethylene glycol)]bisacrylamide, N,N'-methylenebis acrylamide, or N,N'-(1,2-dihydroxyethylene) bisacrylamide.

In another aspect, the shell monomers can be 2-aminoethyl methacrylate (AEMA), 2-aminoethyl acrylamide, 2-hydroxyethyl methacrylate, 2-hydroxyethyl acrylamide, 2-hydroxyethyl acrylate, methoxy polyethyleneglycol methacrylate, methoxy polyethyleneglycol acrylamide, methoxy polyethyleneglycol acrylate, 3-hydroxypropyl methacrylate, 2,2-dimethylaminoethyl methacrylate, 2-(2-methoxyethoxy) ethyl 2-methylacrylate, 2,3-dihydroxypropyl methacrylate, or 2-methacryloyloxyethyl phosphorylcholine.

In another aspect, the core preferably acts as a proton sponge and expands at least 10- to 50-fold in volume when exposed to below pH 6.

In another aspect, the present invention provides methods and means for efficient cytosolic delivery of nanocrystal imaging probes for applications including single particle tracking experiments to monitoring protein-protein interactions in live cells for extended periods. The technology to high throughput schemes which may bear relevance to early detection of disease markers from extracted tissues and has the potential to provide the most direct method to date for determining the intracellular biochemistry of inorganic nanomaterials and their respective coatings.

DETAILED DESCRIPTION OF THE PREFERRED EMBODIMENT

Introduction

In one embodiment, a method to deliver nanocrystals to the cytosol of live cells that is both rapid and general. The present technique employs a unique, cationic core-shell polymer colloid that directs nanocrystals to the cytosol of living cells within a few hours of incubation. When vesicles containing nanocrystals transported into the cell by these colloids fuse with lysosomes, the intraorganelle pH decreases causing the colloids to expand in volume due to a proton sponge constructed at their cores. Membrane disruption ensues, leaving nanocrystals free to disperse in the cytosol for imaging experiments.

Figure 1:
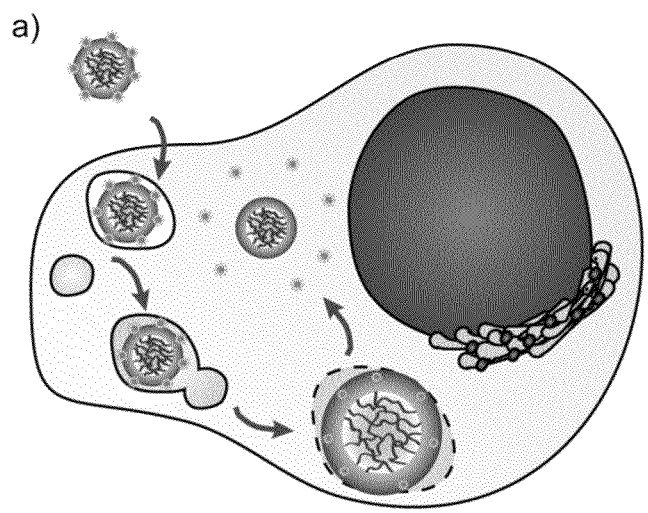
FIG. 1. Delivery of nanocrystals to the cytosol of live cells with cationic core-shell polymer colloids. (a) Suggested mechanism of cellular uptake, trafficking, expansion, and endosomal rupture, leading to cytosolic delivery of nanocrystals. (b) Schematic depiction of cationic core-shell polymer colloids and their constituent monomers.
Figure 1:
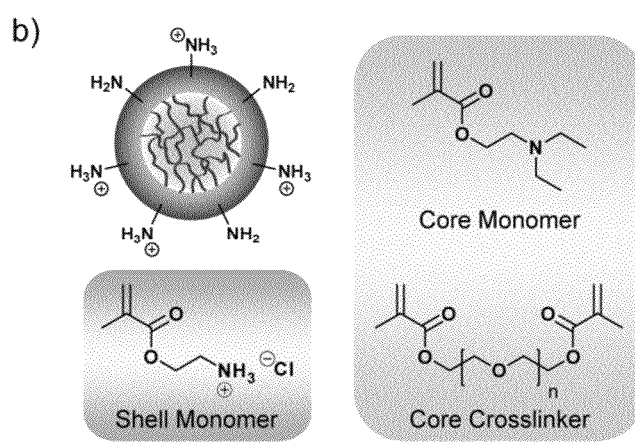
Figure 1:
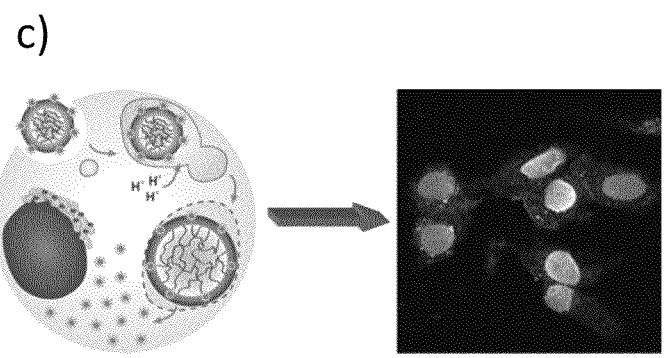

To develop an efficient and general method for targeting nanocrystals to the cytosol and subcellular organelles, we have synthesized proton sponge-based core-shell polymer colloids that are able to bind nanocrystals, transport them into the cell, and release them into the cytosol within a few hours of application (FIG. 1A). Furthermore, we find that picomolar concentrations of quantum dots bound to these colloids are sufficient to give good cytosolic luminescence, with minimal evidence of residual endosomal staining patterns. The overall process is both straightforward and general to a broad range of nanocrystal-based probe designs. This technique may substantially simplify how researchers apply nanocrystals for imaging and diagnostics in live cells.

Definitions

The term "nanocrystal" and "nanoparticle" are used interchangeably, and herein refer to materials typically comprising a core or core-shell configuration, of any shape including spherical, rod, tetrapod, or other shape, and of nanometer size.

The terms "colloid" and "colloidal particle" are used interchangeably herein, and are defined to mean microscopic particles small enough to exhibit collective behavior in solution. The colloidal particles may have a diameter of about 10 nm to 5 µm, and are preferably about 50 nm-1 µm in diameter, and more preferably about 100 nm-350 nm. The particles may be of any shape, but are preferably essentially spherical. In one embodiment, the colloidal particles are nanospheres.

The term "alkyl" herein refers to an aliphatic linear or branched chain univalent groups of the general formula $C_nH_{2n+1}$ derived from aliphatic hydrocarbons such as methyl $CH_3$, ethyl $C_2H_5$, propyl $C_3H_7$, 2-methyl propyl $C_4H_{11}$, and the like or cyclic aliphatic univalent groups of the general formula $C_nH_{2n-1}$ derived from cyclic aliphatic hydrocarbons, such as cyclypropyl $C_3H_5$, cyclopentyl $C_5H_9$ and the like, where n is between 2 and 20.

The term "loading" herein refers to the amount of nanonanocrystals that is encapsulated per milligram of the delivery systems. This may be expressed in terms of µg material/mg delivery system, on average, based on the starting nanocrystal/colloid ratio.

The terms "d", "min", "s" and "rt" used herein refer to days, minutes, seconds, and room temperature, respectively.

DESCRIPTIONS OF THE EMBODIMENTS

In one embodiment, a method to deliver nanoparticles to the cytosol of live cells that is both rapid and general. In one embodiment, the method employs a cationic core-shell polymer colloid that directs nanocrystals to the cytosol of living cells within a few hours of incubation. Referring now to FIG. 1A, the nanocrystals are first conjugated to or contained within the cationic core-shell polymer colloids to form a colloid-nanocrystal conjugate. Upon application or contacting with a cell, the colloid-nanocrystal conjugates are taken up by the cells into vesicles and transported into the cell. The vesicles containing the colloid-nanocrystal conjugates fuse with lysosomes which causes the intraorganelle pH to decrease. The decrease in intraorganelle pH causes the colloid-nanocrystal conjugates to expand in volume and results in membrane disruption. Upon such membrane disruption the nanocrystals are free to disperse in the cytosol.

In some embodiments, a composition comprising a polymer colloid for delivery of materials to the cytosol of live cells. The polymer colloid is preferably a cationic core-shell polymer colloid having a core that exhibits rapid expansion at low intraorganelle pH to facilitate the delivery of luminescent nanocrystal cargo into the cytosol of live cells. To form the colloids, the core monomer and core crosslinker are polymerized in the presence of an initiator. The polymerized core is then reacted with a shell monomer to form a core-shell colloid.

The core of the cationic core-shell polymer colloid comprising a polymer of core monomers, wherein a first core monomer, having the formula $R_1C(CH_2)$—$C(O)$—$R_2$—$R_3$—$N(R_4)R_5$, wherein $R_1$ is H or alkyl, $R_2$ is O or NH, $R_3$ is an alkyl and $R_4$ and $R_5$ are H or alkyl, is crosslinked to a second core monomer (also referred to herein as a crosslinker or crosslinker monomer), having the formula $R_1C(CH_2)$—$C(O)$—$R_2$—$CH_2$—$(CH_2$—$O$—$CH_2)_n$—$CH_2$—$R_2$—$C(O)$—$C(CH_2)$—$R_1$, wherein $R_1$ is H or alkyl, $R_2$ is O or NH, and n is 1 to 50.

Examples of suitable core monomers include but are not limited to 2-(diethylamino)ethyl methacrylate (DEAEMA), 2-(dimethylamino)ethyl methacrylate, 2-(diisopropylamino) ethyl methacrylate, 2-(diethylamino)ethyl acrylate, 2-(dimethylamino)ethyl acrylate, 2-(diisopropylamino)ethyl acrylate, 2-(diethylamino)ethyl acrylamide, 2-(dimethylamino) ethyl acrylamide, or 2-(diisopropylamino)ethyl acrylamide.

Suitable second core monomers include crosslinker monomers such as but are not limited to poly(ethylene glycol) dimethacrylate (PEGDMA), N,N'-[α,ω-diaminopoly(ethylene glycol)]bisacrylamide, N,N'-methylenebisacrylamide, or N,N'-(1,2-dihydroxyethylene)bisacrylamide.

In some embodiments, the ratio of core monomers to core crosslinker monomers is provided as between 200 and 10 to 1. In one embodiment, 1% w/w core crosslinker is polymerized with the core monomer. In a preferred embodiment, the core is intended to act as a proton sponge and expand below pH 6. The core should exhibit at least a 10-fold, and more preferrably a 50-fold increase in volume. Independent of temperature, the present colloids expand dramatically below pH 6, exhibiting up to a 50-fold increase in volume, consistent with recent studies of related hydrogels (See References (12)). This is a direct consequence of the proton sponge core, which becomes charged and solvated at low pH as the core crosslinker monomer's tertiary amines become protonated. Volume expansion exhibited by these cationic core-shell polymer colloids disrupts late endosomal membranes, providing for a mechanism of release by the core-shell colloid of bound or otherwise conjugated nanocrystals into the cytosol of live cells. The increase in volume is concomitant with an increase in the $\zeta$ potential from +7 mV at pH 7.4 to +45 mV at pH 5.5, which may also serve to compromise endosomal membrane integrity in a manner similar to PBAEs. To the best of our knowledge, cationic core-shell colloids such as these have not been employed previously to deliver nanocrystals to the cytosol of live cells nor have they demonstrated applicability to non-phagocytic cells types as described here.

In another embodiment, the colloids can exhibit volume expansion upon a change in temperature (e.g., increase or decrease). It is anticipated that a combination of temperature change in addition to lower than pH 6 exposure will induce proton expansion in the colloids. Such sensitivity also lends the system another measure of control of delivery of nanocrystals to the cytosol.

The initiator for polymerization can be added in varying amounts which results in a range of sizes of colloids. The initiator for polymerization can be a thermal, UV, ionizing radiation, electrochemical, plasma, or redox initiator. In one embodiment, about 20 to 200 mg of a thermal initiator added to about 1.0 of the core monomer and core crosslinker, results in colloids of about 40 nm to 400 nm in size. In one embodiment, the initiator used is ammonium persulfate (APS). For example, if 20 mg of APS is added to a core monomer and crosslinker such as PEGDMA and PDEAEMA, colloids of about 350 nm will be formed. In other embodiments, the initiator can be but is not limited to potassium persulfate, 4,4'-azobis(4-cyanovaleric acid), 2,2'-azobis(2-methylpropionamidine) dihydrochloride, 2,2'-azobis[N-(2-carboxyethyl)-2-methylpropionamidine]hydrate, 2,2'-azobis{2-[1-(2-hydroxyethyl)-2-imidazolin-2-yl]propane}dihydrochloride, or 2,2'-azobis[2-(2-imidazolin-2-yl)propane].

The polymerized core is then reacted with a shell monomer to form a core-shell colloid. In one embodiment, the shell monomer is reacted with the polymerized core in the presence of initiator for about 1.5 hours to form a core-shell colloid.

The shell of the colloid comprising a hydrophilic monomer or a mixture of hydrophilic monomers. In one embodiment, the shell comprising a monomer having the formula $R_1C(CH_2)$—$C(O)$—$R_2$—$R_3$—$N(R_4)R_6$, wherein $R_1$ is H or alkyl, $R_2$ is O or NH, $R_3$ is an alkyl, $R_4$ is H or alkyl, and $R_6$ is H, alkyl, acyl or $C=(NH)NH_2$ and a second shell monomer having the formula $R_1C(CH_2)$—$C(O)$—$R_2$—$CH_2$—$(CH_2$—$O$—$CH_2)_n$—$CH_2$—$R_2$—$C(O)$—$C(CH_2)R_1$, wherein $R_1$ is H or alkyl, $R_2$ is O or NH, and n is 1 to 50, wherein the second core monomer and second shell monomer can be the same or different. Alternatively, the shell comprising a shell monomer having the formula $R_1C(CH_2)$—$CHO$—$R_2$—$R_7$, wherein $R_1$ is H or alkyl, $R_2$ is O or NH, and $R_7$ is H, alkyl, alkanols, oligoethyleneoxide and derivatives thereof, quaternary amino, alkyl phosphonates or alkylsulfonates.

Suitable shell monomers include but are not limited to monomers such as 2-aminoethyl methacrylate (AEMA), 2-aminoethyl acrylamide, 2-hydroxyethyl methacrylate, 2-hydroxyethyl acrylamide, 2-hydroxyethyl acrylate, methoxy polyethyleneglycol methacrylate, methoxy polyethyleneglycol acrylamide, methoxy polyethyleneglycol acrylate, 3-hydroxypropyl methacrylate, 2,2-dimethylaminoethyl methacrylate, 2-(2-methoxyethoxy)ethyl 2-methylacrylate, 2,3-dihydroxypropyl methacrylate, or 2-methacryloyloxyethyl phosphorylcholine.

The polymerization reaction can occur by emulsion polymerization, by inverse emulsion polymerization or by dispersion polymerization. In one embodiment, the colloids were synthesized by surfactant-free emulsion polymerization at 70° C. in water using ammonium persulfate (APS) as the initiator. The PDEAEMA-co-PEGDMA crosslinked proton sponge cores were grown for 3 h, reaching a diameter of ~120 nm, prior to the addition of AEMA for the shell.

One skilled in the art might also prepare the colloids using emulsion, dispersion or inverse-emulsion polymerization. In one embodiment, dispersion can be used to produce colloid particles from sub-micrometer to multi-micrometer sizes; a preferable size range is from 10 nm to 5000 nm, more preferably 50 nm to 1000 nm, and most preferably 100 to 350 nm.

For example, during inverse microemulsion polymerization, a small amount of water can be dispersed into an organic phase and stabilized by surfactants. Sonication before polymerization for a few minutes may insure the correct particle size, which will cover a range of sizes, within the range of about 10 nm to 5 µm, and are preferably about 50 nm-1 µm in diameter, and more preferably about 100 nm-350 nm. The core monomers are polymerized in the aqueous phase and an initiator molecule or radical source. Since polymerization is initiated and contained within water droplets, mainly spherical crosslinked colloids are produced. To adjust particle size, either longer sonication time or larger surfactant concentration may decrease the colloid size There are many nanoprecipitation techniques known to those familiar in the art. Other methods that can be used in the present invention can be devised similar to the methods described in the Examples below.

In another embodiment, the colloids are made into delivery systems such as a small molecule implant, or time-release device or implant. Methods and compositions useful in making or administering an implant or time-release device in vivo are known and used by one having skill in the art. Examples of such methods and compositions are described in U.S. Pat. Nos. 3,976,071; 5,876,452; 7,077,859; 5,021,241, hereby incorporated by reference. For example, the polymers of the invention can be prepared in solid form of a needle or bar-like shape or as a bulk shaped material and administered to the body or implanted into the body by injection or an injection-like method and whereby the bioactive material is released at an effective level for a long period of time after administration After polymerization of the core-shell colloids is complete, the colloids can be purified and stored. The colloids may be suspended or stored in a conventional nontoxic vehicle, which may be solid or liquid, water, saline, or other means which is suitable for maintaining pH, encapsulation of the bioactive material for an extended period of time, sufficient dispersion or dilution of the delivery systems and the overall viability of the delivery systems for their intended use.

Preferably the polymer colloids of the invention are stored dispersed in buffer and sonicated or vortexed for a few minutes to resuspend into solution when needed.

The shell of the colloid can be functionalized to provide further characteristics to the colloids. In some embodiments, the shell monomer comprising a hydrophilic monomer or a mixture of hydrophilic monomers having at least one pendant amine group whereby functional groups can be attached. In some embodiments, the amine group is protected and a functional group is added later. Examples of functional groups include but are not limited to groups such as, guanidine, tetraalkylammonium, zwitterionic monomer, polar monomers, etc. In one embodiment, the shell monomer is functionalized with a guanidine because guanidine is protonated at pH 7.4 and imparts further cationic characteristics to the colloids which enhances interaction with the cell surface. Protonated guanidine groups on the colloid are complementary to cell surface charge.

In another embodiment, signal peptides are attached to the particle. Any suitable signal peptide can be used in the particles of the invention. The peptide should be able to target (i.e., mediate entry and accumulation) a particle to a subcellular compartment and/or organelle of interest. Signal peptides are typically about 5 to about 200 amino acids in length. Suitable signal peptides include, e.g., nuclear localization signal peptides, peroxisome-targeting signal peptides, cell membrane-targeting signal peptides, mitochondrial-targeting signal peptides, and endoplasmic reticulum-targeting signal peptides, and trans-Golgi body-targeting signal peptides. Signal peptides may also target the particles to any cell surface receptor including e.g. epidermal growth factor receptors (EGFR), fibroblast growth factor receptors (FGFR), vascular endothelial cell growth factor receptor (VEGFR), integrins, chemokine receptors, platelet-derived growth factor receptor (PDGFR), tumor growth factor receptors, and tumor necrosis factor receptors (TNF).

Nuclear localization signal peptides typically comprise positively charged amino acids. Endoplasmic reticulum targeting signal peptides typically comprise about 5 to about 10 hydrophobic amino acids. Mitochondria targeting signal peptides are typically about 5 to about 10 amino acids in length and comprise a combination of hydrophobic amino acids and positively charged amino acids. Peroxisome targeting signal peptides include PTS1, a 3 amino acid peptide and PTS2, a 26-36 amino acid peptide. Examples of signal peptide sequences include but are not limited to the following sequences in Table 1.

Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994)).

In another embodiment, a targeting functional group or other cell penetrating peptides to penetrate non-phagocytic cells. For example, targeting functional groups include antibodies, various oligopeptides, or carbohydrate moieties, cell-penetrating peptides can also include oligopeptides such as oligomers of arginine or polymers rich in arginine motifs.

In another embodiment, targeting antibodies are attached to the colloid. Any antibody specific for a target in vivo can be attached to the particle to target and allow colloid delivery of the nanocrystal The colloids are incubated or processed with the nanoparticle or nanocrystal to conjugate, bind to, entrap within, interact or otherwise assemble the nanocrystal particles to the colloids. In one embodiment, the nanocrystals are coated with streptavidin and incubated with the colloids which leads to self-assembly.

Figure 3:
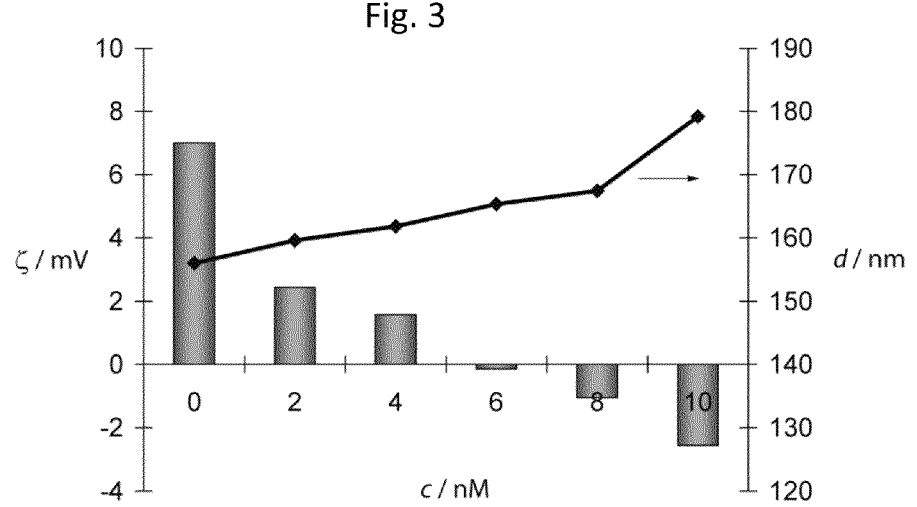
FIG. 3. Changes in surface potential (ζ) and diameter (d) of cationic core-shell polymer colloids charged with QDs in PBS at pH 7.4 at the indicated concentrations (c) as determined by electrokinetic potential measurements and dynamic light scattering.
Figure 10:
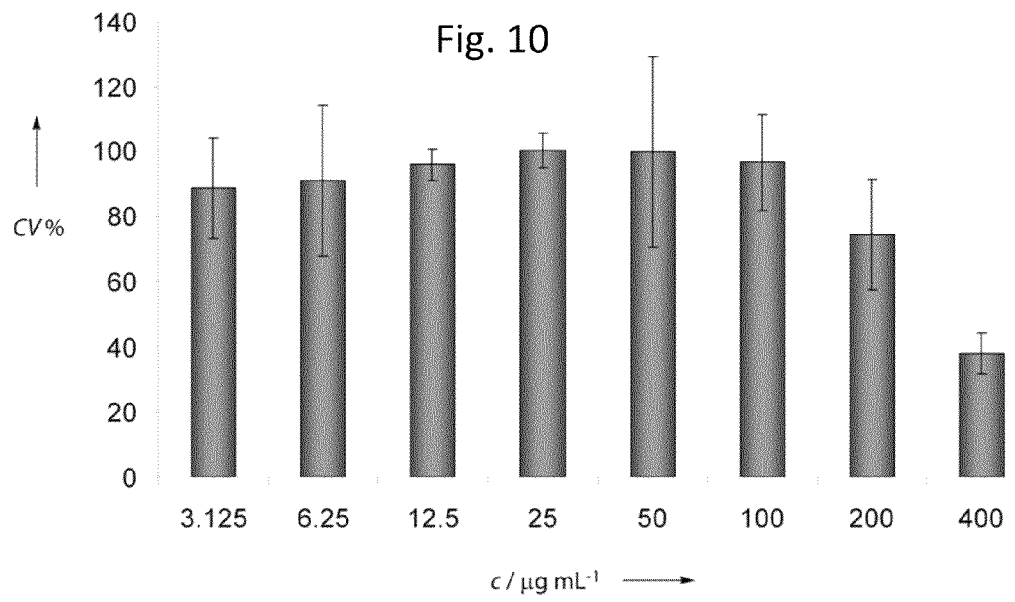
FIG. 10. HeLa cell viability (CV) in the presence of cationic polymer colloids (c=3.125-400 μg mL$^{-1}$) and 5 nM SA-605-QDs as measured by the formazan absorbance at $\lambda$=490 nm following introduction of MTS.

In one embodiment, addition of streptavidin-coated quantum dots (605-SA-QDs, diameter ~20 nm, $\lambda_{em}$=605 nm, $\zeta$=–9 mV in PBS at pH 7.4) to the colloids led to facile self-assembly, presumably through multivalent electrostatic interactions between the ammonium ions on the colloid shell and acidic streptavidin side chains (Scheme 1). After 12 h, the co-assembly showed a monomodal distribution by DLS and, most importantly, quantum dot luminescence was undiminished (data not shown). Increasing the ratio of quantum dots to colloids resulted in a monotonic increase in the diameter of the assembly, from 155 nm to 180 nm, with an inversion of the $\zeta$ potential to negative values observed for quantum dot concentrations exceeding 5 nM (FIG. 3). We anticipated that the internalization of quantum dot-loaded colloids would be optimal when the overall $\zeta$ potential at the surface remained positive. Furthermore, initial cell viability assays (FIG. 10) indicated that cell health was adversely affected for colloid concentrations in excess of 100 μg mL$^{-1}$. Therefore, we pro-

TABLE 1

| Target | Source | Sequence |
|---|---|---|
| Nucleus | SV-40 large T antigen | PPKKKRKVPPKKKRKV (SEQ ID NO: 1) |
| Nucleus | Tat protein of HIV | YGRKKRRQRRR (SEQ ID NO: 2) |
| Endoplasmic Reticulum | | KDELA KDELA KDELA KDEL (SEQ ID NO: 3) |
| Mitochondria | Cytochrome C oxidase | SVTTPLLLRGLTGSARRLPVPRAKIHSL (SEQ ID NO: 4) |
| Peroxisome | | SKLA SKLA SKLA SKLA (SEQ ID NO: 5) |
| Cell Membrane | | KLNPPDESGPCMSCKCVLS (SEQ ID NO: 6) |
| Cell Membrane | GAP-43 | MLCCMRRTKQVEKNDEDQKI (SEQ ID NO: 7) |

Signal peptides can be chemically synthesized or recombinantly produced. In general, the nucleic acid sequences encoding signal peptides and related nucleic acid sequence homologues are cloned from cDNA and genomic DNA libraries or isolated using amplification techniques with oligonucleotide primers. Standard techniques are used for nucleic acid and peptide synthesis, cloning, DNA and RNA isolation, amplification and purification. Basic texts disclosing the general methods of use in this invention include Sambrook et al., ceeded with cell labeling experiments with no greater than 100 μg mL$^{-1}$ of the colloids used in conjunction with less than 5 nM of the streptavidin-coated quantum dots.

An exemplary and preferred photoluminescent component is a nanocrystal of semiconducting materials, such as "quantum dots" (QDs), quantum rods (QRs), quantum dot-quantum rods (QD-QRs) and quantum wires (QWs). QDs, QRs, QD-QRs and QWs have several advantages over conventional fluorescent dyes, including a long luminescent lifetime and near quantitative light emission at a variety of preselected wavelengths. QDs typically contain a semiconductor core of a metal sulfide or a metal selenide, such as zinc sulfide (ZnS), lead sulfide (PbS), or, most often, cadmium selenide (CdSe). Non-heavy metal-based QDs have also been reported. The semiconductor core may be capped with tiopronin or other groups or otherwise varied to modify the properties of the quantum dots, most notably to vary biocompatibility and enhance chemical versatility. The emission wavelengths of nanoparticles may be between about 400 nm and about 2000 nm, including but not limited to the visible range, and the excitation wavelength between about 250 nm and 1900 nm.

QDs typically have diameters of 1 to about 20 nm, depending on the emission wavelength desired, thickness of coating, and the particular application for the nanocrystals. In freeze-fracture electron microscopy characterization, the shadow cast by QDs is evidence of their hard-core structure. One or more QDs can be conjugated to a single nanoscaffold. The number of QDs attached to a core structure may be at least two, at least three, at least four, or 10 or more, 100 or more, or even 1,000 or more, limited in part by the surface area of the nanoparticle core particle, steric effects of adjacent QDs, and the number of functional groups present on the nanocrystal. The QDs on a particular colloid may be of a single color (i.e., single predominant emission wavelength), or of a plurality of colors.

A selected set of QDs may be attached to a colloid in a multiplexed manner to produce nanoparticle labeling reagents with a "bar code," i.e., an emission spectra characterized by particular emission wavelengths and intensities (both relative and absolute). Such labeling reagents can be resolved by spectral unmixing techniques and used for, e.g., (i) multi-color labeling, (ii) multi-color coding, (iii) multiple parameter diagnosis, and the like.

Commercially available (off-shelf) QDs include peak emission at 525 nm, 545 nm, 565 nm, 585 nm, 605 nm, 625 nm, 655 nm, 705 nm, and 800 nm.

In a preferred embodiment, the inorganic nanoparticle core comprises a fluorescent semiconductor nanocrystal or metal nanoparticle. The term "nanoparticle" as used herein refers to a particle whose size is measured in nanometers. Nanoparticles include, e.g., semiconductor nanocrystals, metal nanocrystals, hollow nanoparticles, carbon nanospheres. The nanoparticles typically have a diameter in the range of about 1 nm to about 20 nm, preferably less than about 10, 12, 14, 16, 17, or 20 nm. The nanoparticles can be of any shape including, rods, wire, arrows, teardrops and tetrapods (see, e.g., Alivisatos et al., *J. Am. Chem. Soc.* 122:12700-12706 (2000)). Other suitable shapes include, e.g., square, round, elliptical, triangular, rectangular, rhombal and toroidal. The nanoparticles typically comprise a shell and a core. Typically the shell material will have a bandgap energy that is greater than the bandgap energy of the core material. In some embodiments, the shell material has an atomic spacing close to that of the core material. The term "monolayer" refers to each atomic layer of the shell material around the core. Each monolayer increases the diameter of the shell material, and increases the emission and total fluorescence of the core. The shell may further comprise a hydrophilic material (e.g., any compound with an affinity for aqueous materials such as $H_2O$). Nanoparticles include, e.g., semiconductor nanocrystals.

The nanoparticle core and the shell may comprise the same material or different materials. The nanoparticle shell may further comprise a hydrophilic coating or another group that facilitates conjugation of a chemical or biological agent or moiety to a nanoparticle (i.e., via a linking agent). In some embodiments, the semiconductor nanocrystals comprise a nanoparticle core upon which a hydrophilic coating has been deposited.

The nanoparticle core and the shell may comprise, e.g., an inorganic semiconductive material, a mixture or solid solution of inorganic semiconductive materials, or an organic semiconductive material. Suitable materials for the nanoparticle core and/or shell include, but are not limited to semiconductor materials, carbon, metals, and metal oxides. In a preferred embodiment, the nanoparticles comprise a semiconductor nanocrystal. In a particularly preferred embodiment, the semiconductor nanocrystals comprise a CdSe core and a ZnS shell which further comprises a hydrophilic coating.

The nanoparticle core typically has a diameter of about 1, 2, 3, 4, 5, 6, 7, or 8 nm. The nanoparticle shell typically has thickness of about 1, 2, 3, 4, 5, 6, 7, or 8 nm and a diameter of about 1 to about 10, 2 to about 9, or about 3 to about 8 nm. In a preferred embodiment, the nanoparticle core is about 2 to about 3 nm in diameter and the nanoparticle shell is about 1 to about 2 nm in thickness.

Suitable semiconductor materials for the nanoparticle core and/or shell include, but are not limited to, elements of Groups I, II, III, VI, V or VI or lanthanides and binary or ternary compounds, alloys or mixtures thereof. In one embodiment, the nanoparticle core comprising a binary compound of Group II-VI such as ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, and the like, or a Group III-V compound such as GaN, GaP, GaAs, GaSb, InN, InP, InAs, InSb, and the like, or Group IV (Ge, Si, and the like). Suitable metals and metal oxides for the nanoparticle core and/or shell include, but are not limited to, Au, Ag, Cu, Co, Ni, $Fe_2O_3$, $TiO_2$, and the like. Suitable carbon nanoparticles include, but are not limited to, carbon nanspheres, carbon nano-onions, and fullerenes.

In another embodiment, the luminescent nanoparticles can be made from binary or ternary compounds, alloys or mixtures of materials comprising lanthanides. In one embodiment, the luminescent nanoparticle is a nanocrystalline matrix doped with a lanthanide or mixture of lanthanides. Suitable matrices include but are not limited to $NaYF_4$, $ScF_3$, $YF_3$, $LaF_3$, $Y_2O_3$, $LaPO_4$, or $YVO_4$. Suitable dopants include La, Ce, Pr, Nd, Pm, Sm, Eu, Gd, Tb, Dy, Ho, Er, Tm, and/or Yb.

In another embodiment, the luminescent nanoparticles comprising metals such as gold, silver, platinum, tin, or other chalcogenic compounds, etc. In one embodiment, nanoparticles comprising gold plasmonic structures.

Semiconductor nanocrystals can be made using any method known in the art. For example, methods for synthesizing semiconductor nanocrystals comprising Group III-V semiconductors or Group II-VI semiconductors are set forth in, e.g., U.S. Pat. Nos. 5,751,018; 5,505,928; and 5,262,357. The size of the semiconductor nanocrystals can be controlled during formation using crystal growth terminators U.S. Pat. Nos. 5,751,018; 5,505,928; and 5,262,357. Methods for making semiconductor nanocrystals are also set forth in Gerion et al., *J. Phys. Chem.* 105(37):8861-8871 (2001) and Peng et al., *J. Amer. Chem. Soc.*, 119(30):7019-7029 (1997) hereby incorporated by reference.

The semiconductor nanocrystals may further comprise a hydrophilic coating (e.g., a coating of hydrophilic materials or stabilizing groups) to enhance the solubility of the nanocrystals in an aqueous solution. Typically the hydrophilic coating is about 0.1, 0.25, 0.5, 0.75, 1, 2, 3, 4, 5, 6, 7, 8, 9, or 10 nm thick. Suitable hydrophilic materials include, e.g., SiO, $SiO_2$, polyethylene glycol, ether, mecapto acid and hydrocarbonic acid, and dihydroxylipoic acid (DHLA). Suitable stabilizing groups include, e.g. positively or negatively charged groups or groups that facilitate steric repulsion. In a preferred embodiment, the hydrophilic coating is a silica shell (e.g., comprising $SiO_2$). Methods of silanizing semiconductor nanocrystals are well known in the art and are described in, e.g., Gerion et al., Chemistry of Materials, 14:2113-2119 (2002). Other methods for generating water-soluble semiconductor nanocrystals are described in, e.g., Mattoussi et al., Physica Status Solidi B, 224(1):277-283 (2001) and Chan et al., Science, 281:2016-2018 (1998).

In a preferred embodiment, the nanoparticle hydrophilic coating comprises a silica shell having a thickness of about 0.5 to about 5, about 1 to about 4, or about 2 to about 3 nm. Preferably the silica shell is amorphous and porous. Silica shells can be deposited on the core or the shell of the semiconductor nanocrystal using the methods described in, e.g., Alivisatos et al., Science, 281:2013-2016 (1998) and Gerion, et al., J. Phys. Chem. 105(37):8861-8871 (2001). In a preferred embodiment, the semiconductor nanocrystals have core/shell configuration of $CdSe/ZnS/SiO_2$ wherein the layers are about 25/5/50 Å respectively from the center of the core.

The absorption and emission properties of semiconductor nanocrystals offer several advantages over dye molecules which have narrow wavelength bands of absorption (e.g., about 30-50 nm) and broad wavelength bands of emission (e.g., about 100 nm) and broad tails of emission (e.g., another 100 nm) on the red side of the spectrum. Both of these properties of dyes impair the ability to use a plurality of differently colored dyes when exposed to the same energy source.

In contrast, the semiconductor nanocrystals are capable of absorbing and emitting radiation (i.e., luminescing) in response to a broad range of wavelengths, including the range from gamma radiation to microwave radiation. The semiconductor nanocrystals are also capable of emitting radiation within a narrow wavelength band of about 50, 40, 30, 20, or 10 nm or less. Thus, a single energy source can be used to excite the luminescence of a plurality of semiconductor nanocrystals, each of which comprises a different material. The plurality of semiconductor nanocrystals can easily be distinguished following excitation because each semiconductor nanocrystal will emit only a narrow wavelength band.

The wavelength band emitted from the semiconductor nanocrystal is related to the physical properties (e.g., size, shape, and material), of the semiconductor nanocrystal. More particularly, the wavelength band emitted by the semiconductor nanocrystals may be affected by (1) the size of the core; (2) the size of the core and the size of the shell; (3) the composition of the core and shell. For example, a semiconductor nanocrystal comprised of a 3 nm core of CdSe and a 2 nm thick shell of CdS will emit a narrow wavelength band of light with a peak intensity wavelength of 600 nm. In contrast, a semiconductor nanocrystal comprised of a 3 nm core of CdSe and a 2 nm thick shell of ZnS will emit a narrow wavelength band of light with a peak intensity wavelength of 560 nm. As another example, when a 1-10 monolayer thick shell of CdS is epitaxially grown over a core of CdSe, there is a dramatic increase in the room temperature photoluminescence quantum yield. Thus, one of skill in the art will appreciate that any of the physical properties of the semiconductor nanocrystals can be modified to control the wavelength band of the semiconductor nanocrystal and the corresponding targeted nanoplex.

One of skill in the art will appreciate that a number of variables can be adjusted to selectively manipulate wavelength band emitted by the semiconductor nanocrystals. For example, the composition of the semiconductor nanocrystal core or shells can be varied and the number of shells around the core of the semiconductor nanocrystal can be varied. In addition, semiconductor nanocrystals comprising different core materials, but the same shell material can be synthesized. Semiconductor nanocrystals comprising the same core material, but the different shell materials can also be synthesized.

Figure 2:
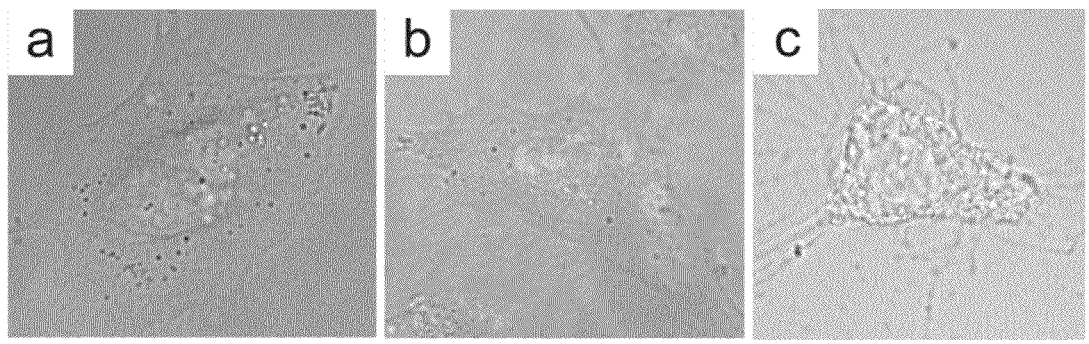
FIG. 2. Vector mediated internalization of 605-SA-QDs (5 nM) by HeLa cells using various pH-responsive polymer colloids. Nanocrystal staining patterns were observed using wide-field fluorescence microscopy. Bright field images are shown for three vectors with the nanocrystal channel overlayed in order to visualize the fate of nanocrystals using the different chemical compositions and thus mechanisms for delivery. Acid degradable Ac-Dex based vectors (A) gave weak signals in the 605-QD channel suggesting poor internalization efficiency for this cell type. Improved cell uptake was observed for vectors comprised of Ac-Dex blended with 10% w/w PBAEs (B), however the staining pattern was characteristically punctuate suggesting vesicular confinement. In contrast, cationic PDEAEMA-co-PEGDMA core-PAEMA shell polymer vectors with low pH-mediated volume expansion showed diffuse cytosolic staining (C) suggesting nanocrystals no longer reside in vesicles.

After incubation or processing the colloids with the nanocrystals, which results with, in one embodiment, cationic polymeric colloids coated with nanocrystals. The nanocrystal-cationic core-shell polymer colloid comprising a core polymer having an outer shell and a nanocrystal conjugated to or coating the shell which can now be used for live cell imaging. In one embodiment, for live cell imaging, cells are incubated with 50-100 μg $mL^{-1}$ of cationic polymeric colloids coated with quantum dots. Luminescence in the cytosol first is observable between 1-4 hours past the incubation period It is shown in the examples that in contrast to charge neutral colloids based on acetalated dextrans or their blends with PBAEs, cells incubated with quantum dot-loaded (PDE-AEMA-co-PEGDMA)-graft-PAEMA core-shell colloids showed diffuse luminescence in the cytosol after as little as 4 h (FIG. 2C). Rapid delivery appears to be characteristic for these colloids over other polymer carriers, which often require between 24-48 h to disrupt endosomes[4e,8,10]. Potential mechanisms for this colloid-mediated endosomal disruption are being explored and include mechanical breach of endosomal bilayers by explosive colloid expansion, osmotic shock caused by hydration of cations within the previously hydrophobic core, or rapid changes electrochemical potential due to the movement of anions to the core.

In one embodiment, a means for efficient cytosolic delivery of nanocrystal imaging probes for applications including single particle tracking experiments to monitoring protein-protein interactions in live cells for extended periods. The technology to high throughput schemes which may bear relevance to early detection of disease markers from extracted tissues and has the potential to provide the most direct method to date for determining the intracellular biochemistry of inorganic nanomaterials and their respective coatings.

EXAMPLE 1

Preparation and Use of Cationic Core-Shell Colloids for Cytosolic Delivery of Nanocrystal Compositions Nanocrystals are typically taken up by live cells via endocytosis and the large majority remains trapped in endosomes, unable to reach the cytosol (Reference 5). Staining patterns corresponding to one or more nanocrystals confined to endosomes are characteristically punctate and often bright enough to obscure nanocrystal luminescence elsewhere in the cytosol from those that may have adventitiously escaped. Nanocrystals have been directly introduced into the cytosol using microinjection or electroporation; although, these methods are exceptionally labor intensive, low throughput, and frequently incur cell death or stress. Passive delivery strategies, including those mediated by polymers (e.g., lipofectamine or PLGA) or nanocrystal surface passivation with cell penetrating peptides (e.g, the TAT peptide derived from HIV-1), have demonstrated some decrease in endosomal staining; however, the process is slow and the prevalence of residual puncta may still interfere with sensitive single molecule imaging experiments.

To develop an efficient and general method for targeting nanocrystals to the cytosol and subcellular organelles, we synthesized proton sponge-based core-shell polymer colloids that are able to bind nanocrystals, transport them into the cell, and release them into the cytosol within a few hours of application (FIG. 1A). Furthermore, we find that picomolar concentrations of quantum dots bound to these colloids are sufficient to give good cytosolic luminescence, with minimal evidence of residual endosomal staining patterns. The overall process is both straightforward and general to a broad range of nanocrystal-based probe designs. We expect the technique to substantially simplify how researchers apply nanocrystals for imaging and diagnostics in live cells.

In an effort to develop a more efficient and general method for the delivery of nanocrystals to the cytosol of non-phagocytic cells, we designed cationic core-shell polymer colloids containing a pH-buffering proton sponge using poly(ethylene glycol) dimethacrylate (PEGDMA, MW=330 Da) crosslinked poly(2-(diethylamino)ethyl methacrylate) (PDEAEMA) for the core and poly(2-aminoethyl methacrylate) (PAEMA) for the shell (FIG. 1B). The colloids were synthesized by surfactant-free emulsion polymerization at 70° C. in water using ammonium persulfate (APS) as the initiator. The PDEAEMA-co-PEGDMA crosslinked proton sponge cores were grown for 3 h, reaching a diameter of ~120 nm, prior to the addition of AEMA for the shell.

Materials. Dextran from *Leuconostoc mesenteroides* (MW~9×10$^3$-1.1×10$^4$ Da, Sigma), 2-methoxypropene (Aldrich), p-toluenesulfonic acid (Aldrich, recrystallized from benzene), 2-(N,N-diethylamino)ethyl 2-methacrylate (DMAEMA) (Aldrich, inhibitor removed using a short path column of basic alumina), 2-aminoethyl 2-methacrylate hydrochloride (AEMA) (Aldrich), poly(ethylene glycol) dimethacrylate (PEGDMA) (MW~330) and ammonium persulfate (APS) (Aldrich) were used as supplied unless described otherwise. Anhydrous solvents of the highest possible purity were used for all chemical transformations. Buffers and media were purchased from Sigma-Aldrich or prepared from biochemical grade salts and ultra-high purity water (Millipore) and sterile-filtered prior to use. Acetalated dextran (Ac-Dex) (FIG. 7a, $t_{1/2}$=0.4 h) was synthesized according to Fréchet et al[1] *Proc. Nat. Acad. Sci. U.S.A.* 2009, 106, 5497. For blend particles, a poly(β-aminoester) (PBAE) (FIG. 7b, $M_n$=4.3×10$^4$ Da, $M_w$=1.2×10$^5$ Da, PDI=2.8) was synthesized according to Langer et al. QDot 605 ITK Streptavidin conjugates (Invitrogen) were used along with 3,3'-dioctadecyloxacarbocyanine perchlorate (DiO) (Invitrogen) and 4',6-diamidino-2-phenylindole (DAPI) (Invitrogen) for confocal fluorescence microscopy experiments. HeLa cells (ATCC# CCL-2) were obtained from ATCC (Manassas, Va.) and grown according to guidelines.

Experimental Methods. Preparation of polymeric nanoparticles via nanoprecipitation. Ac-Dex (10 mg) or its blend with PBAE (up to 10% w/w) was dissolved in dimethyl sulfoxide (1 mL). This solution was added dropwise to a scintillation vial containing MilliQ water (20 mL) stirring at 900 rpm. After 6 h, particles were purified via tangential flow filtration (MicroKos TFF filters, Spectrum Laboratories) against MilliQ water and used immediately for subsequent analysis or further experiments.

Preparation of cationic polymer colloids. A volume of water (10 mL) containing DMAEMA (1.00 mL, 5 mmol) and PEGDMA (10 mg, 30 µmol) was degassed at 70° C. prior to the introduction ammonium persulfate (20 mg, 88 µmol) in degassed water (100 µL). After 3 h, an aliquot was taken to determine the size of the PDMAEMA-co-PPEGDMA core before a solution of AEMA (40 mg, 241 µmol) in degassed water (50 µL) was added to the reaction mixture to grow the shell. After an additional 1.5 h, the reaction mixture was cooled to room temperature. The suspension of colloids was dialyzed against PBS at pH 7.4 using tangential flow filtration (MicroKos TFF filters, Spectrum Laboratories) and subsequently stored at 4° C. The characterization of these materials follows.

Figure 7:
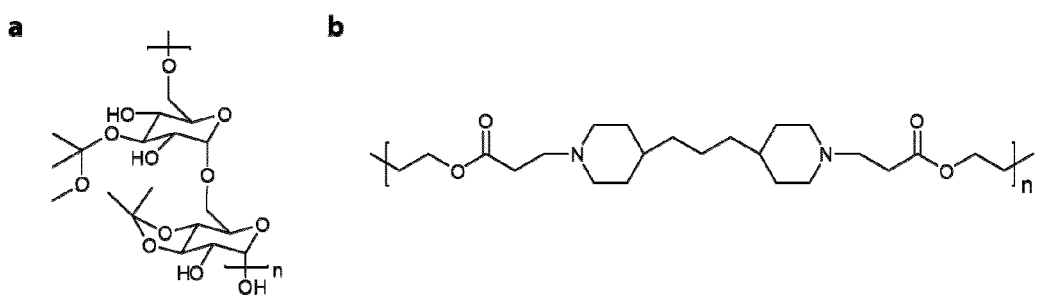
FIG. 7. Chemical structures of various pH-responsive linear polymers evaluated in the present study for the cytosolic delivery of luminescent nanocrystals in live cells: a) Fréchet's 'acetalated' dextran (n~65) bearing both cyclic (DS~85) and acyclic acetals (DS~58); and b) a poly(β-aminoester) (PBAE) 'proton sponge' described by Langer and coworkers.

Colloids were purified by dialysis and characterized by dynamic light scattering (DLS) at physiologically relevant neutral and acidic pH (FIG. 7). Particle size analysis by dynamic light scattering (DLS). DLS measurements were obtained using a Malvern Zetasizer Nano ZS. Cationic core-shell polymer colloids were suspended in PBS at pH 7.4 or acetate buffer at pH 5.5 (1 mg mL$^{-1}$) and equilibrated at either 25° C. or 37° C. for 10 minutes prior to analysis. Data are reported as volume fractions (V %) for an observed particle diameter (d). Zeta potential measurements (see FIG. 2) were performed by diluting one of the above mixtures 1:10 in MilliQ water. Data were collected until a count of 10$^5$ was reached.

Independent of temperature, these colloids expand dramatically below pH 6, exhibiting up to a 50-fold increase in volume, consistent with recent studies of related hydrogels[12]. This is a direct consequence of the proton sponge core, which becomes charged and solvated at low pH as the PDEAEMA's tertiary amines become protonated. We and others have demonstrated that the volume expansion exhibited by these cationic core-shell polymer colloids disrupts late endosomal membranes possibly providing for a novel mechanism of release for bound nanocrystals into the cytosol of live cells. The increase in volume is concomitant with an increase in the ζ potential from +7 mV at pH 7.4 to +45 mV at pH 5.5, which may also serve to compromise endosomal membrane integrity in a manner similar to PBAEs. To the best of our knowledge, cationic core-shell colloids such as these have not been employed previously to deliver nanocrystals to the cytosol of live cells nor have they demonstrated applicability to non-phagocytic cells types as described here.

EXAMPLE 2

Screening Acetalated Dextran and Polyurethane Based Compositions for Cytosolic Delivery Noting that membrane impermeability and endosomal sequestration prevent nanocrystals from reaching the cytosol of live intact cells, we hypothesized that delivery could be conferred if endosomal disruption were to be triggered by some physical or chemical stimulus. pH-Responsive polymer colloids have previously been shown to mediate the delivery of membrane impermeable macromolecules—including drugs, proteins and nucleic acids—to intracellular targets in phagocytic dendritic cells and macrophages by facilitating endocytosis and then disrupting late endosomes at low intraorganelle pH (ca. 5.0-5.5) (Reference 7). For example, acetalated dextran-based colloids (Reference 8) (Ac-Dex) undergo pH-triggered decomposition in endolysosomal compartments, putatively resulting in osmotic shock and endosomal rupture, while colloids comprised of proton-sponges[9]— e.g., poly(β-amino esters) (Reference 10) (PBAEs)—do so presumably via electrostatic destabilization of the membrane. An initial screen of microparticulate colloids (diameters~250 nm) prepared from these polymers and their blends as delivery agents for protein-coated CdSe/ZnS core-shell quantum dots (QDs) to HeLa cells, which are a non-phagocytic cell line, showed either weak staining suggestive of poor cellular uptake, or puncta suggestive of sequestration within endosomes (FIGS. 2A & 2B, respectively). Other formulations along these lines from acid degradable polyurethanes and acid degradable PBAEs were likewise poor delivery agents or had little propensity for nanocrystal adsorption (data not shown). We concluded that charge-neutral colloids, as prepared from Ac-Dex or acid degradable polyurethanes, were not efficient carriers of nanocrystals to non-phagocytic cell types. Furthermore, when the surface potential of these polymer vectors was manipulated to have partial cationic character, e.g., via blending of Ac-Dex with 10% w/w PBAEs, the internalization efficiency improved; however, the intracellular trafficking pathways seem not to give rise to the same low-pH driven endolysosomal release pathways that is typically observed for phagocytic cell types. Our results are consistent with recent work pointing to the importance of both cell type (i.e. phagocytic vs. non-phagocytic) and colloid surface charge in mediating efficient uptake and cytosolic delivery of macromolecular cargo (Reference 11). Thus, while there are many lessons to glean from the vast literature on polymer carriers of membrane impermeable macromolecular cargo, most have not demonstrated broad applicability to non-phagocytic cell types (i.e., the majority of cells) nor have any demonstrated efficient delivery of nanocrystals to the cytosol of live cells, free from endosomal confinement, which is a prerequisite for most advanced bioimaging schemes

EXAMPLE 3

Figure 9:
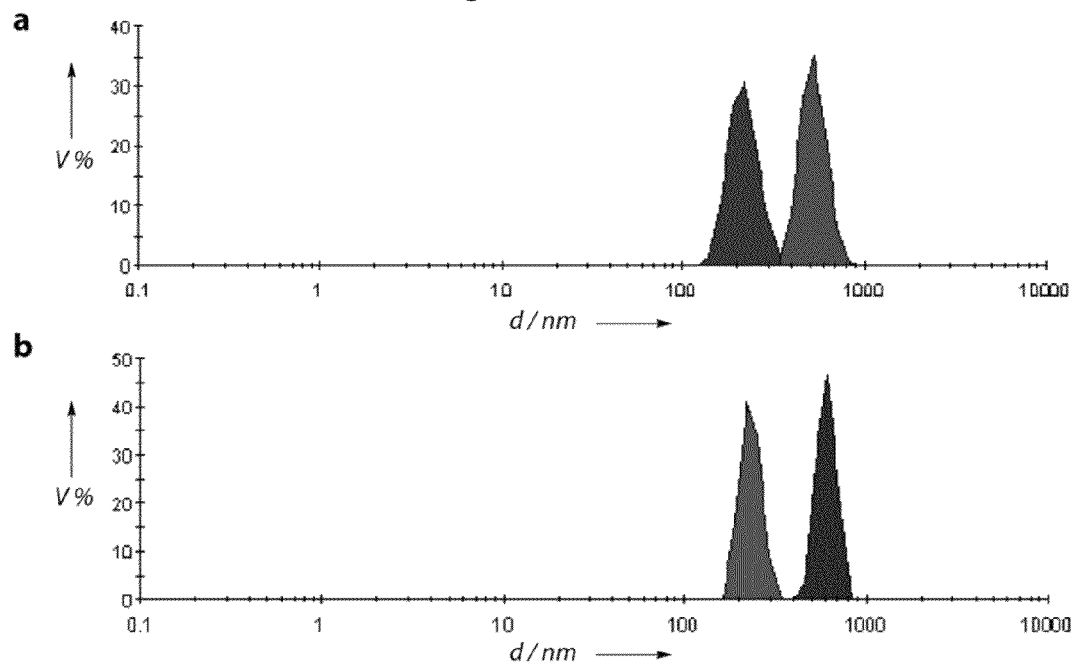
FIG. 9. Particle size analysis of SA-605-QDs non-specifically adsorbed to various polymer colloids: a) Ac-Dex particles prepared by nanoprecipitation (darker gray, $d_{avg}$=237 nm) form aggregates (gray, $d_{avg}$=552 nm) upon addition of SA-605-QDs; b) Ac-Dex blends with PBAEs (gray, $d_{avg}$=234 nm) likewise tend towards aggregation (dark gray, $d_{avg}$=608 nm) upon assembly.

Cytosolic Delivery of Coated-QD Compositions Using Cationic Polymer Colloids Adsorption of SA-605-Qdots to polymer colloids. SA-605-QDs (2-10 nM) were incubated with polymer colloids (50-1000 μg mL$^{-1}$) in Dulbecco's PBS (D-PBS) (Aldrich) at 4° C. on a rotating carousel for 12 hours prior to analysis. The assembly behavior of SA-605-QDs with colloids prepared from acetalated dextran or its blend with PBAE are shown in FIG. 9, while that for the cationic polymer colloids appear as FIG. 2 along with zeta potential analysis.

Figure 8:
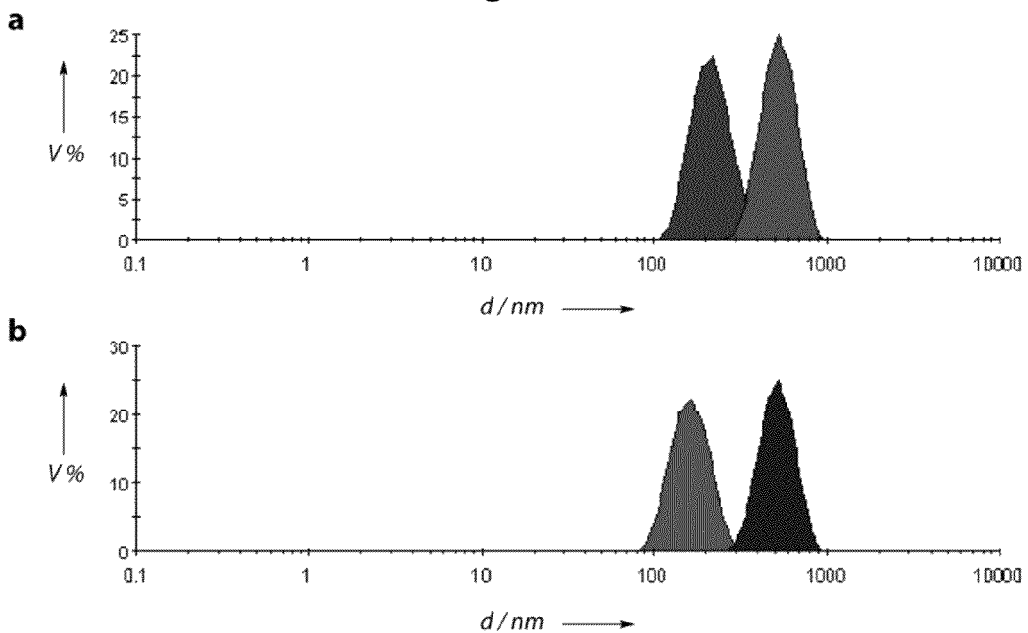
FIG. 8. Particle size analysis of PDEAEMA-co-PEGDMA/PAEMA core-shell colloids: a) T=25° C. at pH 7.4 (darker gray, $d_{avg}$=192 nm) and pH 5.5 (gray, $d_{avg}$=481 nm); and b) T=37° C. at pH 7.4 (gray, $d_{avg}$=145 nm) and pH 5.5 (dark gray, $d_{avg}$=481 nm).

Addition of streptavidin-coated quantum dots (605-SA-QDs, diameter ~20 nm, $\lambda_{em}$=605 nm, ζ=−9 mV in PBS at pH 7.4) to the colloids led to facile self-assembly, presumably through multivalent electrostatic interactions between the ammonium ions on the colloid shell and acidic streptavidin side chains (Scheme 1). After 12 h, the co-assembly showed a monomodal distribution by DLS and, most importantly, quantum dot luminescence was undiminished (data not shown). Increasing the ratio of quantum dots to colloids resulted in a monotonic increase in the diameter of the assembly, from 155 nm to 180 nm, with an inversion of the ζ potential to negative values observed for quantum dot concentrations exceeding 5 nM (FIG. 3). We anticipated that the internalization of quantum dot-loaded colloids would be optimal when the overall ζ potential at the surface remained positive. Furthermore, initial cell viability assays (FIG. 8) indicated that cell health was adversely affected for colloid concentrations in excess of 100 μg mL$^{-1}$. Therefore, we proceeded with cell labeling experiments with no greater than 100 μg mL$^{-1}$ of the colloids used in conjunction with less than 5 nM of the streptavidin-coated quantum dots.

For live cell imaging, HeLa cells were incubated with 50-100 μg mL$^{-1}$ of cationic polymeric colloids coated with quantum dots, or with an equivalent concentration of quantum dots alone. In contrast to charge neutral colloids based on acetalated dextrans or their blends with PBAEs, cells incubated with quantum dot-loaded (PDEAEMA-co-PEGDMA)-graft-PAEMA core-shell colloids showed diffuse luminescence in the cytosol after as little as 4 h (FIG. 2C). Rapid delivery appears to be characteristic for these colloids over other polymer carriers, which often require between 24-48 h to disrupt endosomes (References 4e,8,10). Potential mechanisms for this colloid-mediated endosomal disruption are being explored and include mechanical breach of endosomal bilayers by explosive colloid expansion, osmotic shock caused by hydration of cations within the previously hydrophobic core, or rapid changes electrochemical potential due to the movement of anions to the core.

To conduct live cell confocal fluorescence microscopy, briefly the methods were: HeLa cells (~10$^5$) in DMEM-FBS complete medium were plated onto 35 mm uncoated, glass-bottomed culture dishes (MatTek) and incubated overnight. Cells were then exposed to SA-605-QDs (0-5 nM) in the absence or in the presence of a polymer colloid (25-1000 μg mL$^{-1}$) along with DiO (2.5 μg mL$^{-1}$) at 37° C. for up to 4 h in DMEM-FBS complete medium. Cells were rinsed with D-PBS (3×1 mL) and DMEM-FBS complete medium (3×1 mL) before incubating for up to an additional 12 h at 37° C. Prior to imaging, samples were exposed to DAPI (400 nM) for 15 minutes, and then rinsed D-PBS (3×1 mL) and kept in phenol-red free DMEM-FBS. Fluorescence and brightfield images of labeled cells and controls were acquired using an Olympus FV1000 Spectral Confocal IX81 inverted optical microscope equipped with a 60X/1.42 oil objective. The samples were excited at λ=405 nm (for DAPI and SA-605-Qdot channels) and λ=488 nm (for DiO channel). Acquired images were processed with Olympus software.

Figure 4:
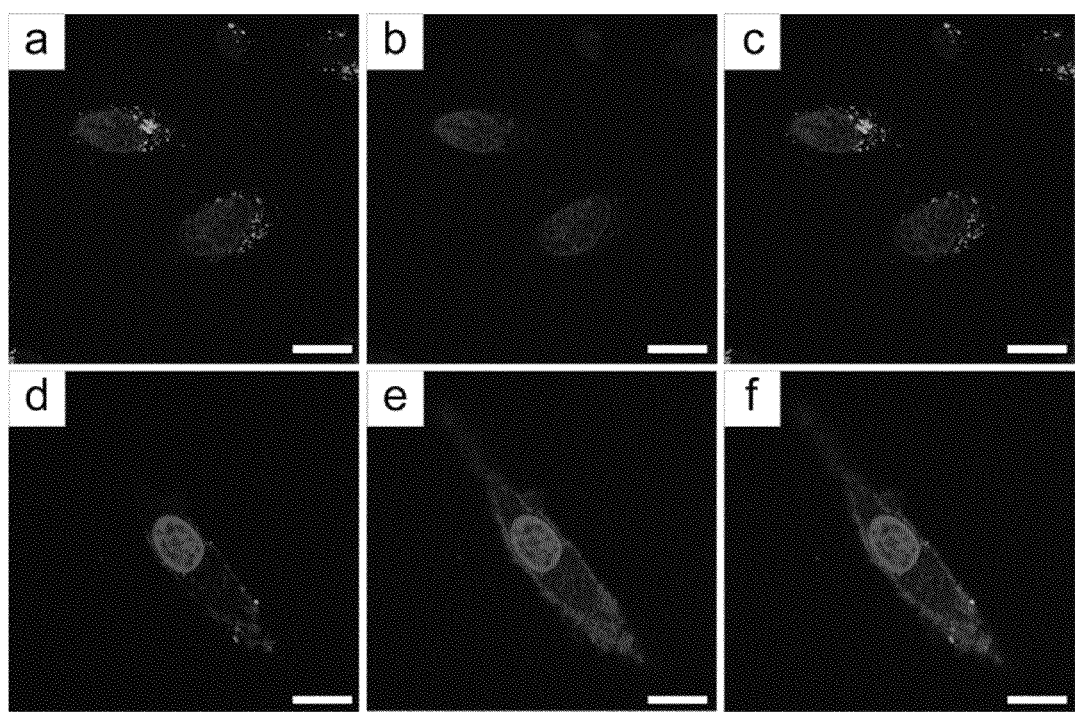
FIG. 4. Confocal fluorescence microscopy determines the intracellular fate of nanocrystals delivered to live HeLa cells. HeLa cells incubated with 500 pM 605-SA-QDs in the absence of polymeric colloids show poor labeling efficiency (a-c): (a) nuclear (DAPI) and endosomal (DiO) fluorescence; (b) nuclear and QD signals; and (c) an overlay of these two images. HeLa cells incubated with 500 pM 605-SA-QDs in the presence of polymer colloids, on the other hand, show a high degree of cytosolic labeling without residual punctuate endosomal staining patterns (d-f): (d) nuclear and endosomal fluorescence; (e) nuclear and QD signals; and (f) an overlay of these two images. All images were captured and processed identically, as described in Supporting Information. Scale bar is 5 μm.
Figure 11:
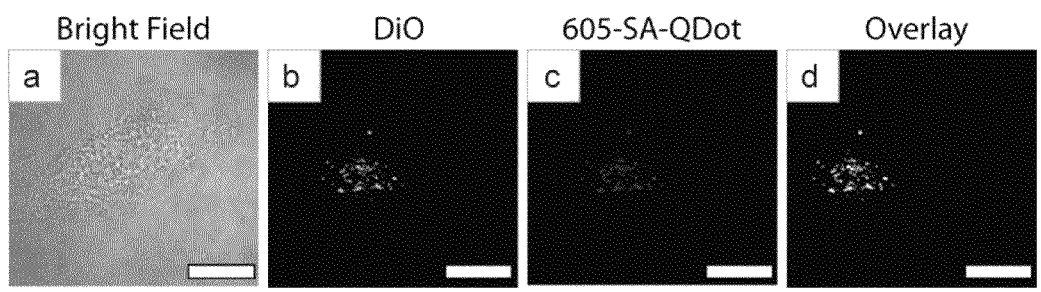
FIG. 11. Internalization of 605-SA-QDs (5 nM) by HeLa cells. Endosomes were stained with the membrane tracer dye DiO (B, green channel). The staining pattern of the nanocrystals (C, red channel) in the cytosol appeared punctuate. Near exclusive co-localization (D, yellow) in the green and red channels supports the claim that the large majority of nanocrystals fail to reach the cytosol, remaining sequestered in vesicles upon internalization. Scale bar=5 µm.

Results. The extent to which the cationic polymer colloids affected the subcellular localization of internalized quantum dots was investigated with confocal fluorescence microscopy and colocalization with known organelle stains. In these experiments, HeLa cells were exposed to the lipophilic membrane tracer dye 3,3'-dioctadecyloxacarbocyanine perchlorate (DiO, $\lambda_{em}$=501 nm) to visualize endosomes, as well as the nuclear stain 4',6-diamidino-2-phenylindole (DAPI, $\lambda_{em}$=461 nm). In control experiments without the polymer colloids, we did not observe accumulation of quantum dots in HeLa cells at sub-nanomolar concentrations (FIG. 4A-C); although endosomes were readily observed as indicated by the punctate staining pattern in the DiO channel (FIGS. 4A & C, green). This points to the efficacy with which our DiO-based staining protocol allows for the visualization of endosomes over the time period of nanocrystal entry to the cell. At higher concentrations of quantum dots (e.g., 5 nM), their internalization was pronounced but confined to vesicular compartments, as evidenced by strong colocalization in the DiO and 605-SA-QD signals (FIG. 11, yellow). This endosomal sequestration persisted even after 12 h following incubation, indicating relatively little self-mediated escape or disruption of endosomal membranes by the quantum dots themselves. In contrast, the cationic polymer colloid-mediated delivery of quantum dots featured both intense and diffuse perinuclear staining patterns as well as weak colocalization with DiO labeled endosomes (FIG. 4D-F). In the few instances where strong DiO colocalization was observed with quantum dots (FIG. 4F, yellow), they were largely abutting the cell membrane, possibly suggesting a fraction of endosomes slow to acidify or ongoing internalization of colloids adsorbed to the cell surface. Shorter incubation times or lower concentrations of quantum dots both gave less intense labeling in the cytosol, offering an efficient means of controlling the number of nanocrystals introduced into cells for single particle tracking and other applications where a low degree of labeling is desirable.

While fluorescence images are a critical gauge of cellular labeling techniques, variations in cell type, microscope settings, image processing, and interpretation make quantitative comparisons difficult. Therefore, we employed flow cytometry to quantify the labeling efficiency and possible toxicity imparted by the cationic polymer colloid or the quantum dots themselves.

Briefly the flow cytometry methods were: HeLa cells were cultured in DMEM-FBS complete medium in 6-well plates (FALCON) and were labeled as described above. The labeled cells were washed with D-PBS (3×1 mL) and harvested with 0.25% trypsin/EDTA (Sigma). DMEM-FBS complete medium (2 mL) was used to inactivate the trypsin and the labeled cells were pelleted by centrifugation at 1000 rpm for 8 minutes, discarding the supernatant. The resulting pellets were washed by resuspending in D-PBS containing 1% w/w BSA (2 mL) and subsequent centrifugation. The pelleted cells were finally resuspended in PBS/1% BSA prior to analysis. Flow cytometry was performed on a BD Biosciences FACS Aria Flow Cytometer. Fluorescence signals from individual labeled cells (10,000 events in total) were obtained by exciting at $\lambda=405$ nm and monitoring the emission using a 605/40 band-pass filter. Data were acquired using FACSDiva v. 6.0 and processed using FloJo v. 7.5. Contour maps of the forward scatter (FS) and side scatter (SS) data accumulated for the flow cytometry experiments described herein and are given in FIG. 12.

Figure 5:
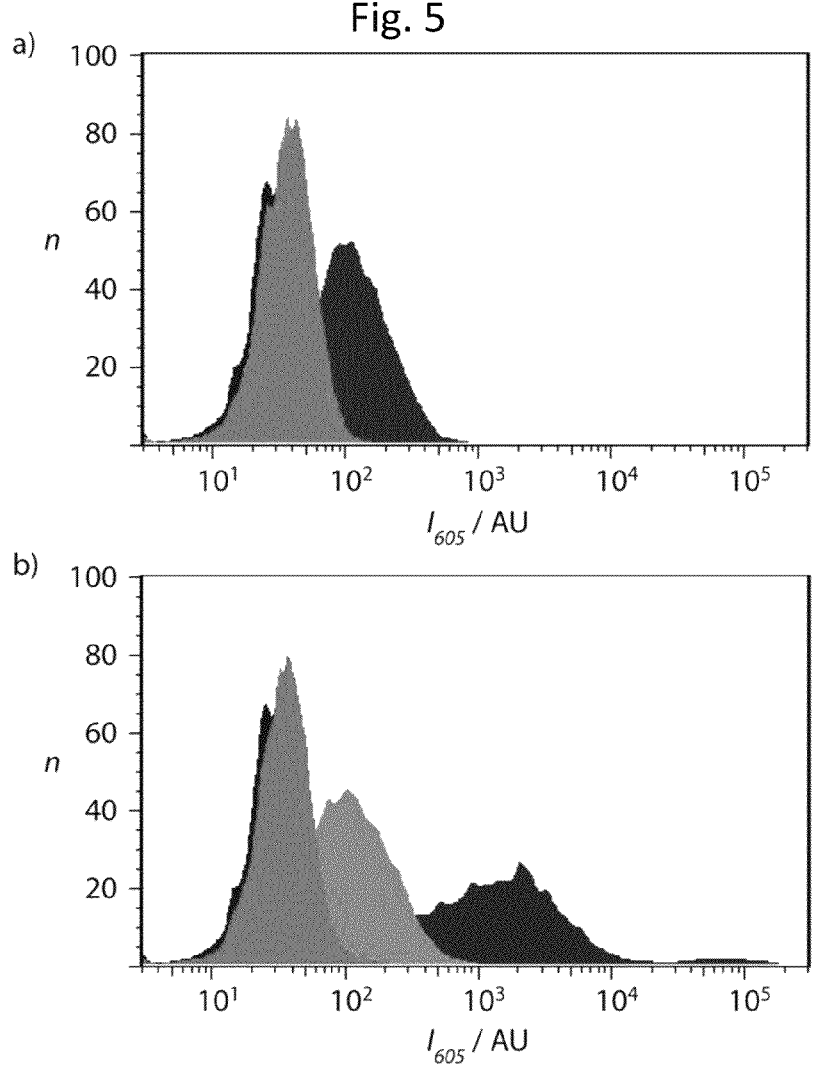
FIG. 5. Quantitative assessment of nanoparticle uptake by flow cytometry of HeLa cells incubated with 605-SA-QDs or 605-SA-QD/polymer colloids: (a) HeLa cells alone (dark gray peak behind gray peak), incubated with 50 pM (gray), 500 pM (light gray, mostly obscured), or 5 nM (dark gray to right of gray peak) 605-SA-QDs; and (b) Cells alone (dark gray peak behind gray peak), incubated with 50 pM (gray), 500 pM (light gray) or 5 nM (dark gray to right of light gray peak) 605-SA-QD/polymer colloids. The distributions reflect the number of cells (n) with a given luminescence intensity ($I_{605}$) and are reported for a representative sampling of 10,000 cells for each measurement.
Figure 6:
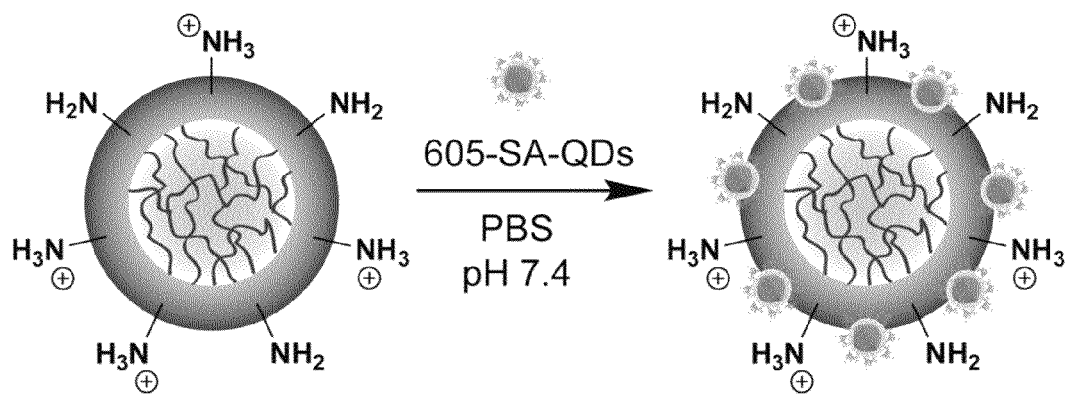
FIG. 6. Adsorption of anionic streptavidin-coated quantum dots onto the surface of cationic core-shell polymer colloids via non-specific electrostatic interactions.

Results. HeLa cells were incubated with quantum dots either in the absence or in the presence of the polymer vector as in previous experiments. In the absence of the polymer vector, there was no increase in 605-nm emission over background in cells treated with 50 or 500 pM quantum dots alone (FIG. 5A), in good agreement with the confocal fluorescence microscopy experiments that pointed to poor internalization efficiency at sub-nanomolar concentrations of probes. At a quantum dot concentration of 5 nM, labeling was clearly observed, with the increase in the geometric mean fluorescence 2.5-fold above background (FIG. 5A, dark gray), although the confocal fluorescence imaging indicate that the probes remained sequestered in endosomes under these labeling conditions (FIG. 11). By comparison, the quantum dot delivery efficiency to HeLa cells was markedly improved in the presence of polymer colloids, and the extent of labeling was commensurate with increasing concentrations of the probes. In the highest concentration tested (5 nM), the increase in the geometric mean fluorescence above background was approximately 20-fold. These results were also consistent with the confocal fluorescence microscopy experiments where the degree of cytosolic staining was determined by the initial concentration of the probes and to a lesser extent the incubation time.

EXAMPLE 4

Toxicity of Cationic Core-Shell Colloids

Figure 12:
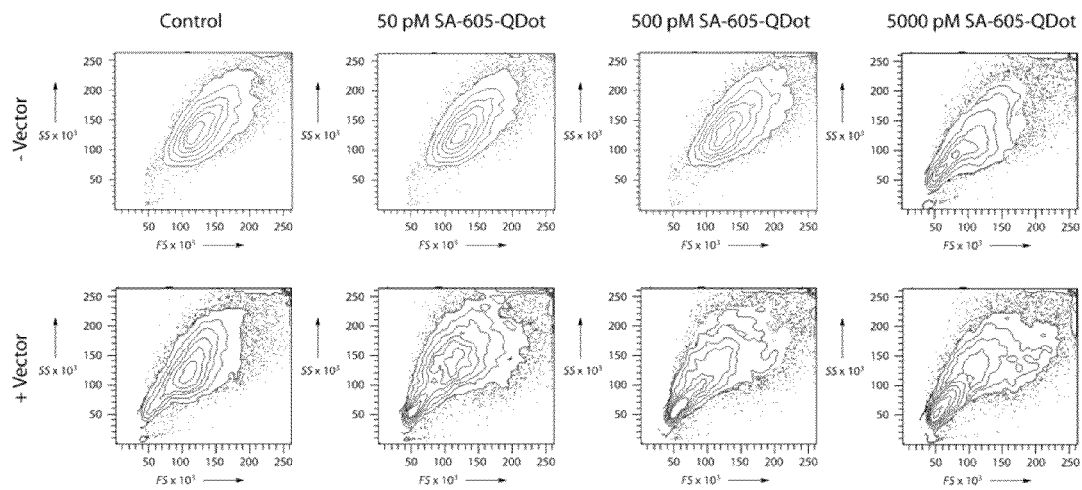
FIG. 12. Flow cytometer light scatter contour plots for experiments reported in the main text (see FIG. 5). The forward scatter (FS, proportional to cell size) and side scatter (SS, proportional to cell complexity or granularity) data indicate a single population of viable HeLa cells is present. Significant deviations from the control samples with respect to both cell size and internal complexity is associated with the cytosolic delivery of increasing levels of SA-605-QDs.

As a preliminary, qualitative measure of toxicity, the scatter plots from the flow cytometry experiments indicated that the presence of increasing amounts of quantum dots in the cytosol led to a decrease in both the average size of the HeLa cells and the degree of internal complexity (or granularity—e.g., fewer subcellular compartments, including endosomes), suggesting that the directed cytosolic delivery of these particular quantum dots to live cells had a pronounced effect on cell physiology (FIG. 12).

Cytotoxicity. Cytotoxicity for Ac-Dex based particles or its blends with PBAEs against HeLa cells have been described elsewhere. The cytotoxicity of PDMAMA-co-PEGDMA-graft-PAEMA cationic polymer colloids or their assemblies with SA-605-QDots was evaluated using a MTS colorimetric assay (CellTiter 96 AQ$_{ueous}$ Non-Radioactive Cell Proliferation Assay, Promega). HeLa cells ($5\times10^4$) were inoculated into a 96-well tissue culture plate (FALCON) with 100 µL of complete media (DMEM supplemented with FBS, 10% v/v) and incubated for 24 h at 37° C. The media was subsequently exchanged for complete media containing the polymer colloid (3.125-400 µg mL$^{-1}$) and SA-605-QDs (0 or 5 nM). The cells were incubated for up to 4 h at 37° C. and analyzed according to the manufacturer's instructions using a SpectraMax Plus 384 Spectrophotometer (Molecular Devices).

In control experiments, neither colloid alone nor quantum dots alone showed similar effects. Previous work has not yielded a consensus on nanocrystal cell toxicity or its possible origins[13], which may arise from phenomena as varied as heavy metal leaching from the nanocrystal, specific physiological responses to the quantum dot surface coatings, or the nature of synthetic nanomaterials themselves. These initial results point to the opportunity to use these cationic polymer vectors in conjunction with flow cytometry as well as genomic and proteomic analyses to establish how and to what extent these luminescent nanocrystals affect specific aspects of cell biology. Given the efficiency of delivery for nanometer-scale objects to the cytosol as shown here, other nanoparticles may also be explored for their toxicity and downstream effects on cell physiology.

For live cell imaging with quantum dots and other nanoscale probes, their complacent sequestration in vesicles has been commonplace and a persistent challenge to overcome. We have shown here that quantitative release from endosomes is afforded by first assembling them to our pH-responsive cationic core-shell polymer colloids before introducing them to cells. The process is technically very simple, and affords cytosolic delivery in only a few hours after incubation. The methodology is demonstrated for a non-phagocytic cell line, which is generally recognized to be more difficult, granting researchers the option of pursuing multiplexed imaging experiments with a broader range of cells. As it is amenable to high throughput schemes, we envision a myriad of possible applications in cell and cancer biology, nanomedicine and medical diagnostics. The efficiency of delivery also suggests that these colloids should be useful in addressing nagging questions about nanocrystal toxicity to cells.

EXAMPLE 5

Effect of Guanidinylation on Nanocrystal Cationic Core-Shell Colloids

HeLa cells incubated with colloids (25 µg mL$^{-1}$) loaded with streptavidin-coated 605-QDots (5 nM) for 1 hr. Cells were washed and given fresh media. After four hours of further incubation, flow cytometry was performed to determine the extent of labeling afforded by colloids of different sizes and surface chemistries shown in Table 2 below:

TABLE 2

| Colloidal Delivery Vector | Mean Fluorescence Intensity |
|---|---|
| Amine Formulation A (diameter = 120 nm) | 630 |
| Amine Formulation B (diameter = 155 nm) | 885 |
| Amine Formulation C (diameter = 350 nm) | 1104 |
| Guanidinylated particles prepared from A | 705 |
| Guanidinylated particles prepared from B | 1531 |
| Guanidinylated particles prepared from C | 3851 |

References

[1] a) Berridge, M. J.; Lipp, P.; Bootman, M. D. *Nat. Rev. Mol. Cell. Biol.* 2000, 1, 11; b) Zhang, J.; Campbell, R. E.; Ting, A. Y.; Tsien, R. Y. *Nat. Rev. Mol. Cell. Biol.* 2002, 3, 906; c) Jan, L. Y.; Siegelbaum, S. A. *Curr. Opin. Neurobiol.* 2005, 15, 253; d) Jorgensen, C.; Linding, R. *Curr. Opin. Genetics Dev.* 2010, 20, 15; E) Lee, K. H.; Lee, S.; Lee, W. Y.; Yang, H. W.; Heo, W. D. *Proc. Nat. Acad. Sci. U.S.A.* 2010, 107, 3412.

[2] a) Yarden, Y.; Sliwkowski, M. X. *Nat. Rev. Mol. Cell. Biol.* 2001, 2, 127; b) Wu, X.; Liu, H.; Liu, J.; Haley, K. N.; Treadway, J. A.; Larson, J. P.; Ge, N.; Peale, F.; Bruchez, M. P. *Nat. Biotechnol.* 2003, 21, 41; c) Gao, X.; Cui, Y.; Levenson, R. M.; Chung, L. W. K.; Nie, S, *Nat. Biotechnol.* 2004, 22, 969.

[3] a) Alivisatos, A. P. *Science* 1996, 271, 933; b) Bruchez, M.; Moronne, M.; Gin, P.; Weiss, S.; Alivisatos, A. P. *Science* 1998, 281, 2013; c) Chan, W. C. W.; Nie, S. *Science* 1998, 281, 2016; d) Michalet, X.; Pinaud, F.; Lacoste, T. D.; Dahan, M.; Bruchez, M. P.; Alivisatos, A. P.; Mitchell, P. *Nat. Biotechnol.* 2001, 19, 1013; e) Michalet, X.; Pinaud, F.; Lacoste, T. D.; Dahan, M.; Bruchez, M. P.; Alivisatos, A. P.; Weiss, S. *Single Molecules* 2001, 2, 261; f) Parak, W. J.; Gerion, D.; Pellegrino, T.; Zanchet, D.; Micheel, C.; Williams, S. C.; Boudreau, R.; Gros, M. A. L.; Larabell, C. A.; Alivisatos, A. P. *Nanotechnology* 2003, 14, R15; g) Alivisatos, A. P. *Nat. Biotechnol.* 2004, 22, 47; h) So, M. -K.; Xu, C.; Loening, A. M.; Gambhir, S. S.; Rao J. *Nat. Biotechnol.* 2006, 24, 339; i) Weissleder, R.; Kelly, K.; Sun, E. Y.; Shtatland, T.; Josephson, L. *Nat. Biotechnol.* 2005, 23, 1418; j) Somers, R. C.; Bawendi, M. G.; Nocera, D. G. *Chem. Soc. Rev.* 2007, 36, 579; k) Resch-Genger, U.; Grabolle, M.; Cavaliere-Jaricot, S.; Nitschke, R.; Nann, T. *Nat. Methods* 2008, 5, 763.

[4] a) Stephens, D. J.; Pepperkok, R.; *Proc. Nat. Acad. Sci. U.S.A.* 2001, 98, 4295; b) Michalet, X.; Pinaud, F. F.; Bentolila, L. A.; Tsay, J. M.; Doose, S.; Li, J. J.; Sundaresan, G.; Wu, A. M.; Gambhir, S. S.; Weiss, S. *Science* 2005, 307, 538; c) Chen, X.; K is, A.; Zettl, A.; Bertozzi, C. R. *Proc. Nat. Acad. Sci. U.S.A.* 2007, 104, 8218; d) Ruan, G.; Agrawal, A.; Marcus, A. I.; Nie, S. *J. Am. Chem. Soc.* 2007, 129, 14759; e) Kim, B. Y. S.; Jiang, W.; Oreopoulos, J.; Yip, C. M.; Rutka, J. T.; Chan, W. C. W. *Nano Lett.* 2008, 8, 3887.

[5] Brandenburg, B.; Zhuang, X. *Nat. Rev. Microbiol.* 2007, 5, 197.

[6] a) Jaiswal, J. K.; Mattoussi, H.; Mauro, J. M.; Simon, S. M. *Nat. Biotechnol.* 2003, 21, 47; b) Derfus, A. M.; Chan, W.; Bhatia, S. *Adv. Mater.* 2004, 16, 961; c) Rozenzhak, S. M.; Kadakia, M. P.; Caserta, T. M.; Westbrook, T. R.; Stone, M. O.; Naik, R. R. *Chem. Commun.* 2005, 2217; d) Delehanty, J. B.; Medintz, I. L.; Pons, T.; Brunel, F. M.; Dawson, P. E.; Mattoussi, H. *Bioconjugate Chem.* 2006, 17, 920; e) Duan, H.; Nie, S. *J. Am. Chem. Soc.* 2007, 129, 3333; f) Ruan, G.; Agrawal, A.; Marcus, A. I.; Nie, S. *J. Am. Chem. Soc.,* 2007, 129, 14759; g) Medintz, I. L.; Pons, T.; Delehanty, J. B.; Susumu, K.; Brunel, F. M.; Dawson, P. E.; Mattoussi, H. *Bioconjugate Chem.* 2008, 19, 1785; h) Joo, K.; Lei, Y.; Lee, C.; Lo, J.; Xie, J.; Hamm-Alvarez, S. F.; Wang, P. *ACS Nano* 2008, 2, 1553; i) Rajan, S. S.; Liu, H. Y.; Vu, T. Q. *ACS Nano,* 2008, 2, 153; j) Qi, L.; Gao, X. *ACS Nano,* 2008, 2, 1403; k) Anas, A.; Okuda, T.; Kawashima, N.; Nakayama, K.; Itoh, T.; Ishikawa, M.; Biju, V. *ACS Nano,* 2009, 3, 2419; l) Wu, S.; Han, G.; Milliron, D. J.; Aloni, S.; Altoe, V.; Talapin, D. V.; Cohen, B. E.; Schuck, P. J. *Proc. Nat. Acad. Sci. U.S.A.* 2009, 106, 10917.

[7] a) Bachelder, E. M.; Beaudette, T. T.; Broaders, K. E.; Paramonov, S. E.; Dashe, J.; Fréchet, J. M. J. *Mol. Pharmaceutics.* 2008, 5, 876; b) Paramonov, S. E.; Bachelder, E. M.; Beaudette, T. T.; Standley, S. M.; Lee, C. C.; Dashe, J.; Frechet, J. M. J. *Bioconjugate Chem.* 2008, 19, 911.

[8] a) Bachelder, E. M.; Beaudette, T. T.; Broaders, K. E.; Dashe, J.; Frechet, J. M. J. *J. Am. Chem. Soc.* 2008, 130, 10494; b) Broaders, K. E.; Cohen, J. A.; Beaudette, T. T.; Bachelder, E. M.; Fréchet, J. M. J. *Proc. Nat. Acad. Sci. U.S.A.* 2009, 106, 5497.

[9] a) Lynn, D. M.; Anderson, D. G.; Putnam, D.; Langer, R. *J. Am. Chem. Soc.* 2001, 123, 8155; b) Akinc, A.; Anderson, D. G.; Lynn, D. M.; Langer, R. *Bioconjugate Chem.* 2003, 14, 979; c) Duan, H.; Nie, S. *J. Am. Chem. Soc.* 2007, 129, 3333; d) Yezhelyev, M. V.; Qi, L.; O'Regan, R. M.; Nie, S.; Gao, X. *J. Am. Chem. Soc.* 2008, 130, 9006.

[10] a) Lynn, D. M.; Langer, R. *J. Am. Chem. Soc.* 2000, 122, 10761; b) Akinc, A.; Lynn, D. M.; Anderson, D. G.; Langer, R. *J. Am. Chem. Soc.* 2003, 125, 5316.

[11] a) Davda, J.; Labhasetwar, V. *Int. J. Pharm.* 2002, 233, 51; b) Fischer, D.; Li, Y.; Ahlemeyer, B.; Krieglstein, J.; Kissel, T. *Biomaterials* 2003, 24, 1121; c) Hong, S.; Bielinska, A. U.; Mecke, A.; Keszler, B.; Beals, J. L.; Shi, X.; Balogh, L.; Orr, B. G.; Baker, J. R.; Banaszak Holl, M. M. *Bioconjugate Chem.* 2004, 15, 774; d) Bēma, D.; Freivalds, T.; Buikis, I.; Harju, L. in 14*th Nordic-Baltic Conference on Biomedical Engineering and Medical Physics,* 2008, pp. 598-601; e) Zhang, X.; Jin, Y.; Plummer, M. R.; Pooyan, S.; Gunaseelan, S.; Sinko, P. J. *Mol. Pharmaceutics.* 2009, 6, 836; f) Zhang, S.; Li, J.; Lykotrafitis, G.; Bao, G.; Suresh, S. *Adv. Mater.* 2009, 21, 419; g) Beaudette, T. T.; Cohen, J. A.; Bachelder, E. M.; Broaders, K. E.; Cohen, J. L.; Engleman, E. G.; Fréchet J. M. J. *J. Am. Chem. Soc.* 2009, 131, 10360; h) Scita, G.; Di Fiore, P. P. *Nature* 2010, 463, 464.

[12] a) Amalvy, J. I.; Unali, G.; Li, Y.; Granger-Bevan, S.; Armes, S. P.; Binks, B. P.; Rodrigues, J. A.; Whitby, C. P. *Langmuir* 2004, 20, 4345; Amalvy, J. I.; Wanless, E. J.; Li, Y.; Michailidou, V.; Armes, S. P.; Duccini, Y. *Langmuir* 2004, 20, 8992; Hu, Y.; Litwin, T.; Nagaraja, A. R.; Kwong, B.; Katz, J.; Watson, N.; Irvine, D. J. *Nano Lett.* 2007, 7, 3056; d) You, J. -O.; Auguste, D. T. *Nano Lett.* 2009, 9, 4467; e) Hu, Y.; Atukorale, P. U.; Lu, J. J.; Moon, J. J.; Um, S. H.; Cho, E. C.; Wang, Y.; Chen, J.; Irvine, D. J. *Biomacromolecules* 2009, 10, 756.

[13] a) Derfus, A. M.; Chan, W. C. W.; Bhatia, S, N. *Nano Lett.* 2004, 4, 11; b) Hoshino, A.; Fujioka, K.; Oku, T.; Suga, M.; Sasaki, Y. F.; Ohta, T.; Yasuhara, M.; Suzuki, K.; Yamamoto, K. *Nano Lett.* 2004, 4, 2163; c) Lovrić, J.; Cho, S. J.; Winnik, F. M.; Maysinger, D. *Chem. Biol.* 2005, 12, 1227; d) Kirchner, C.; Liedl, T.; Kudera, S.; Pellegrino, T.; Javier, A. M.; Gaub, H. E.; Stölzle, S.; Fertig, N.; Parak, W. J. *Nano Lett.* 2005, 5, 331; e)

Ryman-Rasmussen, J. P.; Riviere, J. E.; Monteiro-Riviere, N. A. *Nano Lett.* 2007, 7, 1344.

The above examples are provided to illustrate the invention but not to limit its scope. Other variants of the invention will be readily apparent to one of ordinary skill in the art and are encompassed by the appended claims. All publications, databases, and patents cited herein are hereby incorporated by reference for all purposes.

What is claimed is:

1. A nanocrystal-cationic core-shell polymer colloid composition comprising a core having an outer shell and a nanocrystal conjugated to or assembled to the outer shell,
wherein the core is comprised of a polymer of a first core monomer and a second core monomer, wherein the first core monomer, having the formula $R_1C(CH_2)$—$C(O)$—$R_2$—$R_3$—$N(R_4)R_5$, wherein $R_1$ is H or alkyl, $R_2$ is O or NH, $R_3$ is an alkyl, and $R_4$ and $R_5$ are H or alkyl, is crosslinked to the second core monomer, the second core monomer having the formula $R_1C(CH_2)$—$C(O)$—$R_2$—$CH_2$—$(CH_2$—$O$—$CH_2)_n$—$CH_2$—$R_2$—$C(O)$—$C(CH_2)R_1$, wherein $R_1$ is H or alkyl, $R_2$ is O or NH, and n is 1 to 50;
wherein the outer shell is comprised of a polymer of a first and second shell monomers and the first and second core monomers, wherein the first shell monomer has the formula $R_1C(CH_2)$—$C(O)$—$R_2$—$R_3$—$N(R_4)R_6$, wherein $R_1$ is H or alkyl, $R_2$ is O or NH, $R_3$ is an alkyl, $R_4$ is H or alkyl, and $R_6$ is H, alkly, acyl, or $C$=$(NH)_2$, and the second shell monomer has the formula $R_1C(CH_2)$—$C(O)$—$R_2$—$CH_2$—$(CH_2$—$O$—$CH_2)_n$—$CH_2$—$R_2$—$C(O)$—$C(CH_2)R_1$, wherein $R_1$ is H or alkyl, $R_2$ is O or NH, and n is 1 to 50, wherein the second core monomer and second shell monomer can be the same or different, and wherein at least one of the first or second shell monomers further comprises at least one pendant amine group whereby functional groups can be attached.

2. The composition of claim 1, wherein the core monomers are provided as about 167 parts core monomer to 1 part second core monomer crosslinker on a molar basis.

3. The composition of claim 1, wherein the colloids are formed by emulsion, dispersion or inverse-emulsion polymerization.

4. The composition of claim 1, wherein the first or second shell monomer has functional groups attached.

5. The composition of claim 4, wherein the shell monomer functional group comprises a guanidine.

6. The composition of claim 4, wherein the shell monomer functional group can be any polypeptide, antibody or other targeting sequence or agent which allows the colloid to be targeted to a subcellular area.

7. The composition of claim 1, wherein the nanoparticle further comprises functional ligands or coatings.

8. The composition of claim 7, wherein the nanoparticle coating comprises streptavidin.

9. The composition of claim 1, wherein the nanoparticle comprises a nanocrystalline matrix, doped with a suitable lanthanide or mixture of lanthanides.

10. The composition of claim 9, wherein the nanocrystalline matrix comprises $NaYF_4$, $ScF_3$, $YF_3$, $LaF_3$, $LaPO_4$, $YVO_4$, or $Y_2O_3$.

11. The composition of claims 10, wherein said dopants are La, Ce, Pr, Nd, Pm, Sm, Eu, Gd, Tb, Dy, Ho, Er, Tm, and/or Yb.

12. The composition of claim 1, wherein the first core monomer is 2-(diethylamino)ethyl methacrylate (DEAEMA), 2-(dimethylamino)ethyl methacrylate, 2-(diisopropylamino)ethyl methacrylate, 2-(diethylamino)ethyl acrylate (DEAEA), 2-(dimethylamino)ethyl acrylate, 2-(diisopropylamino)ethyl acrylate, 2-(diethylamino)ethyl acrylamide, 2-(dimethylamino)ethyl acrylamide, or 2-(diisopropylamino)ethyl acrylamide.

13. The composition of claim 1, wherein the second core monomer is poly(ethylene glycol) dimethacrylate (PEGDMA), N,N'-[α,ω-diaminopoly(ethylene glycol)] bisacrylamide, N,N'-methylenebisacrylamide, or N,N'-(1,2-dihydroxyethylene)bisacrylamide.

14. The composition of claim 1, wherein the first shell monomer is 2-aminoethyl methacrylate (AEMA), 2-aminoethyl acrylamide, 2-hydroxyethyl methacrylate, 2-hydroxyethyl acrylamide, 2-hydroxyethyl acrylate, methoxy polyethyleneglycol methacrylate, methoxy polyethyleneglycol acrylamide, methoxy polyethyleneglycol acrylate, 3-hydroxypropyl methacrylate, 2,2-dimethylaminoethyl methacrylate, 2-(2-methoxyethoxy)ethyl 2-methacrylate, or 2,3-dihydroxypropyl methacrylate.

15. The composition of claim 1, wherein the core acts as a proton sponge and expands at least 10- to 50-fold in volume when exposed to below pH 6.

16. A method to deliver nanocrystals to the cytosol of live cells comprising the steps of:
- providing a nanocrystal-cationic core-shell polymer colloid composition of claim 1 comprising a core having an outer shell and a nanocrystal conjugated to or assembled to the outer shell,
- exposing a cell to said polymer colloid whereby said cell takes up said polymer colloid in a celluloar vesicle, and
- delivering the nanocrystal into the cell cytosol.

17. The method of claim 16, wherein the delivery step of the nanocrystals occurs by the following mechanism: the colloids fuse with lysosymes, the intraorganelle pH decreases causing the colloids to expand in volume due to a proton sponge constructed at the polymer colloid cores, membrane disruption ensues, and nanocrystals are freed to disperse in the cytosol for imaging experiments.

* * * * *

```
                        SEQUENCE LISTING

<160> NUMBER OF SEQ ID NOS: 7

<210> SEQ ID NO 1
<211> LENGTH: 16
<212> TYPE: PRT
<213> ORGANISM: Artificial sequence
<220> FEATURE:
<223> OTHER INFORMATION: SV40 large T antigen nucleus targeting peptide

<400> SEQUENCE: 1

Pro Pro Lys Lys Lys Arg Lys Val Pro Pro Lys Lys Lys Arg Lys Val
1               5                   10                  15

<210> SEQ ID NO 2
<211> LENGTH: 11
<212> TYPE: PRT
<213> ORGANISM: Artificial sequence
<220> FEATURE:
<223> OTHER INFORMATION: TAT protein of HIV nucleus targeting peptide

<400> SEQUENCE: 2

Tyr Gly Arg Lys Lys Arg Arg Gln Arg Arg Arg
1               5                   10

<210> SEQ ID NO 3
<211> LENGTH: 19
<212> TYPE: PRT
<213> ORGANISM: Artificial sequence
<220> FEATURE:
<223> OTHER INFORMATION: Endoplasmic reticulum targeting peptide

<400> SEQUENCE: 3

Lys Asp Glu Leu Ala Lys Asp Glu Leu Ala Lys Asp Glu Leu Ala Lys
1               5                   10                  15

Asp Glu Leu

<210> SEQ ID NO 4
<211> LENGTH: 28
<212> TYPE: PRT
<213> ORGANISM: Artificial sequence
<220> FEATURE:
<223> OTHER INFORMATION: Cytochrome C oxidase mitochondria targeting
      peptide

<400> SEQUENCE: 4

Ser Val Thr Thr Pro Leu Leu Leu Arg Gly Leu Thr Gly Ser Ala Arg
1               5                   10                  15

Arg Leu Pro Val Pro Arg Ala Lys Ile His Ser Leu
            20                  25

<210> SEQ ID NO 5
<211> LENGTH: 16
<212> TYPE: PRT
<213> ORGANISM: Artificial sequence
<220> FEATURE:
<223> OTHER INFORMATION: Peroxisome targeting peptide

<400> SEQUENCE: 5

Ser Lys Leu Ala Ser Lys Leu Ala Ser Lys Leu Ala Ser Lys Leu Ala
1               5                   10                  15
```

```
<210> SEQ ID NO 6
<211> LENGTH: 19
<212> TYPE: PRT
<213> ORGANISM: Artificial sequence
<220> FEATURE:
<223> OTHER INFORMATION: Cell Membrane targeting sequence

<400> SEQUENCE: 6

Lys Leu Asn Pro Pro Asp Glu Ser Gly Pro Cys Met Ser Cys Lys Cys
1               5                   10                  15

Val Leu Ser

<210> SEQ ID NO 7
<211> LENGTH: 20
<212> TYPE: PRT
<213> ORGANISM: Artificial sequence
<220> FEATURE:
<223> OTHER INFORMATION: GAP-43 cell membrane targeting peptide

<400> SEQUENCE: 7

Met Leu Cys Cys Met Arg Arg Thr Lys Gln Val Glu Lys Asn Asp Glu
1               5                   10                  15

Asp Gln Lys Ile
            20
```